US007053069B2

(12) United States Patent
Lee et al.

(10) Patent No.: US 7,053,069 B2
(45) Date of Patent: May 30, 2006

(54) PHARMACEUTICAL COMPOSITIONS AND METHODS OF USING C-21 MODIFIED EPOTHILONE DERIVATIVES

(75) Inventors: Francis Y. F. Lee, Yardley, PA (US); Thomas A. Haby, Hillsborough, NJ (US); Vijay H. Naringrekar, Paramus, NJ (US); Krishnaswamy S. Raghavan, Cranbury, NJ (US); Miriam K. Franchini, Allentown, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/437,103

(22) Filed: May 13, 2003

(65) Prior Publication Data

US 2004/0053978 A1 Mar. 18, 2004

Related U.S. Application Data

(60) Provisional application No. 60/380,634, filed on May 15, 2002.

(51) Int. Cl.
*A61K 31/715* (2006.01)
*A61K 31/425* (2006.01)
*C08B 37/02* (2006.01)
*C07D 277/30* (2006.01)

(52) U.S. Cl. .................... 514/59; 514/365; 536/51; 548/204

(58) Field of Classification Search ............... 548/204; 536/51; 514/59, 365
See application file for complete search history.

(56) References Cited

U.S. PATENT DOCUMENTS

| | | | |
|---|---|---|---|
| 6,380,227 B1 | 9/2000 | Mutz | |
| 6,194,181 B1 | 2/2001 | Hofmann et al. | |
| 6,204,388 B1 | 3/2001 | Danishefsky et al. | |
| 6,211,412 B1 | 4/2001 | Georg et al. | |
| 6,242,469 B1 | 6/2001 | Danishefsky et al. | |
| 6,262,094 B1 | 7/2001 | Hoefle et al. | |
| 6,316,630 B1 | 11/2001 | Danishefsky et al. | |
| 6,365,749 B1 | 4/2002 | Kim et al. | |
| 6,369,234 B1 | 4/2002 | Danishefsky et al. | |
| 6,380,394 B1 | 4/2002 | Nicolaou et al. | |
| 6,518,421 B1 | 2/2003 | Li et al. | |
| 6,576,651 B1 | 6/2003 | Bandyopadhyay et al. | |
| 6,605,599 B1 | 8/2003 | Vite et al. | |
| 6,635,666 B1 * | 10/2003 | O'Reilly et al. | 514/365 |
| 6,670,384 B1 | 12/2003 | Bandyopadhyay et al. | |
| 6,686,380 B1 | 2/2004 | Lee | |
| 2002/0143038 A1 | 10/2002 | Bandyopadhyay et al. | |
| 2002/0165257 A1 | 11/2002 | Lee | |
| 2003/0073677 A1 | 4/2003 | Lee | |
| 2003/0187039 A1 | 10/2003 | Favreau et al. | |
| 2003/0220378 A1 | 11/2003 | Lee | |
| 2004/0024032 A1 | 2/2004 | Vol et al. | |

FOREIGN PATENT DOCUMENTS

| | | |
|---|---|---|
| DE | 4138042.8 | 5/1993 |
| DE | 19542986.9 | 5/1997 |
| DE | 19639456.2 | 5/1997 |
| DE | 19636343.8 | 3/1998 |
| DE | 19645361.5 | 4/1998 |
| DE | 19645362.3 | 4/1998 |
| DE | 19647580.5 | 5/1998 |
| DE | 19701758 | 7/1998 |
| DE | 19707505.3 | 9/1998 |
| DE | 19713970 | 10/1998 |
| DE | 19720312 | 11/1998 |
| DE | 19821954 | 11/1998 |
| DE | 19726627 | 12/1998 |
| EP | 879 605 | 11/1998 |
| WO | 93/10121 | 5/1993 |
| WO | 97/19086 | 5/1997 |
| WO | 98/08849 | 3/1998 |
| WO | 98/22461 | 5/1998 |
| WO | 98/24427 | 6/1998 |
| WO | 98/25929 | 6/1998 |
| WO | 98/38192 | 9/1998 |
| WO | 98/47891 | 10/1998 |
| WO | 99/01124 | 1/1999 |
| WO | 99/02514 | 1/1999 |
| WO | 99/03848 | 1/1999 |
| WO | 99/07692 | 2/1999 |
| WO | 99/27890 | 6/1999 |
| WO | 99/39694 | 8/1999 |
| WO | 99/42602 | 8/1999 |
| WO | 99/43320 | 9/1999 |

(Continued)

OTHER PUBLICATIONS

Balog, A., et al., "Total Synthesis of (−)-Epothilone A", *Angew. Chem. Int. Ed. Engl.*, vol. 35, No. 23/24, 2801-2803 (1996).

Bertini, F., et al., "Alkenes from Epoxides by Reductive Elimination with Magnesium Bromide-Magnesium Amalgam", *Chem. Commun.*, 144 (1970).

Bollag, D.M., et al., "Epothilones, A New Class of Microtubule-stabilizing Agents with a Taxol-like Mechanism of Action", *Cancer Res.* 55, No. 11, 2325-2333 (1995).

(Continued)

*Primary Examiner*—Johann Richter
*Assistant Examiner*—Ebenezer Sackey
(74) *Attorney, Agent, or Firm*—Gary D. Greenblatt; Anastasia P. Winslow

(57) ABSTRACT

Pharmaceutical compositions containing C-21 modified epothilone derivatives, methods for their preparation and dosing regimen for administration of these epothilone compounds are provided. The compositions are stable and readily prepared for administration by dissolution in aqueous vehicles suitable for intravenous administration. A process for formulating C-21 modified epothilone derivatives for oral and parenteral administration is disclosed.

75 Claims, No Drawings

FOREIGN PATENT DOCUMENTS

| WO | 99/43653 | 9/1999 |
|---|---|---|
| WO | 99/54319 | 10/1999 |
| WO | 99/67252 | 12/1999 |
| WO | 00/00485 | 1/2000 |
| WO | 00/31247 | 6/2000 |
| WO | 00/37473 | 6/2000 |
| WO | WO 00/39276 | 7/2000 |
| WO | 00/49021 | 8/2000 |
| WO | 00/66589 | 11/2000 |

OTHER PUBLICATIONS

Fujisawa, T., et al., "Deoxygenation of Epoxides to Olefins with $FeCl_3$—-BuLi System", *Chem. Lett.*, 883-886 (1974).

Fujiwara, Y., et al., "Reductive Coupling of Carbonyl Compounds to Olefins by Tungsten Hexachloride-Lithium Aluminum Hydride and Some Tungsten and Molybdenum Carbonyls", *J. Org. Chem.*, vol. 43, No. 12, 2477-2479 (1978).

Gladysz, J. A., et al., "Deoxygenation of Epoxides by Metal Atom Cocondensation", *J. Org. Chem.*, vol. 41, No. 22, 3647-3648 (1976).

Hofle, G., et al., "Epothilone A and B—Novel 16-Membered Macrolides with Cytotoxic Activity: Isolation, Crystal Structure, and Conformation in Solution", *Angew. Chem. Int. Ed. Engl.*, vol. 35, No. 13/14, 1567-1569 (1996).

Hofle, G., et al., "N-Oxidation of Epothilone A-C and O-Acyl Rearrangement to C-19 and C-21—Substituted Epothilones", *Angew. Chem. Int. Ed.*, vol. 38, No. 13/14, 1971-1974 (1999).

Inokuchi, T., et al., "Opening of Epoxides to Olefins or Halohydrins with Vanadium(II)-Tetrahydrofuran or Vanadium(III)-Tetrahydrofuran Complexes", *Synlett*, No. 6, 510-512 (1992).

Kowalski. R. J., et al., "Activities of the Microtubule-stabilizing Agents Epothilones A and B with Purified Tubulin and in Cells Resistant to Paclitaxel (Taxol®)" *J. Biol. Chem.*, vol. 272, No. 4, 2534-2541 (1997).

Kupchan, S. M., et al., "Reductive Elimination of Epoxides to Olefins with Zinc-Copper Couple", *J. Org. Chem.*, vol. 36, No. 9, 1187-1190 (1971).

Martin, M. G., et al., "Epoxides as Alkene Protecting Groups. A Mild and Efficient Deoxygenation", *Tetrahedron Letters*, vol. 25, No. 3, 251-254 (1984).

McMurry, J. E., et al., "Reduction of Epoxides to Olefins with Low Valent Titanium", *J. Org. Chem.*, vol. 40, No. 17, 2555-2556 (1975).

McMurry, J. E., et al., "Some Deoxygenation Reactions with Low-Valent Titanium ($TiCl_3/LiAlH_4$)", *J. Org. Chem.*, vol. 43, No. 17, 3249-3254 (1978).

Meng, D., et al., "Remote Effects in Macrolide Formation Through Ring-Forming Olefin Metathesis: An Application to the Synthesis of Fully Active Epothilone Congeners", *J. Am. Chem. Soc.*, vol. 119, No. 11, 2733-2734 (1997).

Nicolaou, K. C., et al., "An Approach to Epothilones Based on Olefin Metathesis", *Angew. Chem. Int. Ed. Engl.*, vol. 35, No. 20, 2399-2401 (1996).

Nicolaou, K. C., et al., "Total Synthesis of Epothilone A: The Macrolactonization Approach", *Angew. Chem. Int. Ed. Engl.*, vol. 36, No. 5, 525-527 (1997).

Nicolaou, K. C., et al., "Designed Epothilones: Combinatorial Synthesis, Tubulin Assembly Properties, and Cytotoxic Action against Taxol-Resistant Tumor Cells", *Angew. Chem. Int. Ed. Engl.*, vol. 36, No. 19, 2097-2103 (1997).

Nicolaou, K.C., et al., "The Olefin Metathesis Approach to Epothilone A and Its Analogues", *J. Am. Chem. Soc.*, vol. 119, No. 34, 7960-7973 (1997).

Nicolaou, K. C., et al., "Total Syntheses of Epothilones A and B via a Macrolactonization-Based Strategy", *J. Am. Chem. Soc.*, vol. 119, No. 34, 7974-7991 (1997).

Nicolaou, K. C., et al., "Synthesis of Epothilones A and B in Solid and Solution Phase", *Nature*, vol. 387, 268-272 (1997).

Nicolaou, K. C., et al., "Synthesis of Epothilones A and B in Solid and Solution Phase" (Correction to *Nature* 387, 268-272 (1997)), *Nature*, 390, 100 (1997).

Raucher, S., et al., "Total Synthesis of (+)-Dihydrocostunolide via Tandem Cope-Claisen Rearrangement", *J. Org. Chem.*, vol. 51, No. 26, 5503-5505 (1986).

Sato, M, et al., "Reduction of Organic Compounds with Low-Valent Niobium ($NbCl_5/NaAlH_4$)", *Chem. Letters*, 157-160 (1982).

Schinzer, D., et al., "Total Synthesis of (−)-Epothilone A", *Angew. Chem. Int. Ed. Engl.*, vol. 36, No. 5, 523-524 (1997).

Schobert, R., et al., "Reduction and Isomerization of Oxiranes and α-Diazoketones by Various Early Transition Metallocenes", *Synlett*, vol. 8, 465-466 (1990).

Sharpless, K. B., et al., "Lower Valent Tungsten Halides. A New Class of Reagents for Deoxygenation of Organic Molecules", *J. Amer. Chem. Soc.*, vol. 94, No. 18, 6538-6540 (1972).

Su, D.-S., et al., "Total Synthesis of (−)-Epothilone B: An Extension of the Suzuki Coupling Method and Insights into Structure-Activity Relationships of the Epothilones", *Angew. Chem. Int. Ed. Engl.*, vol. 36, No. 7, 757-759 (1997).

Su, D.-S., et al., "Structure-Activity Relationships of the Epothilones and the First In Vivo Comparison with Paclitaxel", *Angew. Chem. Int. Ed. Engl.*, vol. 36, No. 19, 2093-2096 (1997).

Victory, S. F., et al., "Relative Stereochemistry and Solution Conformation of the Novel Paclitaxel-Like Antimitotic Agent Epothilone A", *Bioorg. Med. Chem. Letts.*, vol. 6., No. 7, 893-898 (1996).

Winkler, J. D., et al., "A Model For The Taxol (Paclitaxel)/Epothilone Pharmacophore", *Bioorg. Med. Chem. Letts.*, vol. 6, No. 24, 2963-2966 (1996).

Yang, Z., et al., "Total Synthesis of Epothilone A: The Olefin Metathesis Approach", *Angew. Chem. Int. Ed. Engl.*, vol. 36, No. 1/2, 166-168 (1997).

Bollag, D., et al., "Epothilone, A New Structural Class of Microtubule Stabilizer", Abstract, *Proc. Am. Assoc. Cancer Res.*, vol. 36, 86 Meet. 454 (1995).

Bollag, D., "Epothilones: Novel Microtubule-Stabilising Agents", *Expert Opin. Invest. Drugs*, vol. 6, No. 7, 867-873 (1997).

Bertinato, P., et al., "Studies Toward a Synthesis of Epothilone A: Stereocontrolled Assembly of the Acyl Region and Models for Macrocyclization", J. Org. Chem., vol. 61, No. 23, 8000-8001 (1996).

*Chemical & Engineering News*, "Epothilone Epiphany: Total Syntheses", vol. 74, No. 52, 24-26 (1996).

*Chemical & Engineering News*, "First Total Synthesis of Epothilone B", vol. 75, No. 13, 23 (1997).

*Chemical & Engineering News*, "Solid-Phase Epothilone Synthesis Used to Create Analog Library", vol. 75, No. 20, 33 (1997).

Claus, E., et al., "Synthesis of the C1-C9 Segment of Epothilons", *Tetrahedron Lett.*, vol. 38, No. 8, 1359-1362 (1997).

De Brabander, J., et al., "Towards a Synthesis of Epothilone A: Rapid Assembly of the C1-C6 and C7-C12 Fragments", *Synlett*, vol. 7, 824-826 (1997).

Gabriel, T. and Wessjohann, L., "The Chromium-Reformatsky Reaction: Asymmetric Synthesis of the Aldol Fragment of the Cytotoxic Epothilons from 3-(2-Bromoacyl)-2-Oxazolidinones", *Tetrahedron Lett.*, vol. 38, No. 8, 1363-1366 (1997).

Gerth, K., et al., "Epothilons A and B: Antifungal and Cytotoxic Compounds from *Sorangiusm cellulosum* (Myxobacteria) Production, Physico-chemical and Biological Properties", *J. Antibiotics*, vol. 49, No. 6, 560-563 (1996).

Marshall, A., "Total Synthesis of Epothilone", *Nature Biotechnology*, vol. 15, No. 3, 205 (1997).

Meng, D., et al., "Studies Toward a Synthesis of Epothilone A: Use of Hydropyran Templates for the Management of Acyclic Stereochemical Relationships", *J. Org. Chem.*, vol. 61, No. 23, 7998-7999 (1996).

Meng, D., et al., "Total Syntheses of Epothilones A and B", *J. Am. Chem. Soc.*, vol. 119, No. 42, 10073-10092 (1997).

Mensching, S. and Kalesse, M., "Generation of Thiazoles by Column Dehydrogenation of Thiazolidines with $MnO_2$", *J. Prakt. Chem.*, vol. 339, No. 1, 96-97 (1997).

Mulzer, J. and Mantoulidis, A., "Synthesis of the C(1)-C(9) Segment of the Cytotoxic Macrolides Epothilon A and B", *Tetrahedron Lett.*, vol. 37, No. 51, 9179-9182 (1996).

Nicolaou, K., et al., "Chemistry, Biology and Medicine of Selected Tubulin Polymerizing Agents", *Pure Appl. Chem.*, vol. 71, No. 6, 989-997 (1999).

Nicolaou, K., et al., "Total Synthesis of Epothilone E and Related Side-chain Modified Analogues Via a Stille Coupling Based Strategy", *Bioorg. Med. Chem.*, vol. 7, No. 5, 665-697 (1999).

Schinzer, D., et al., "Studies Towards the Total Synthesis of Epothilones: Asymmetric Synthesis of the Key Fragments", *Chem. Eur. J.*, vol. 2, No. 22, 1477-1482 (1996).

Taylor, R. and Haley, J., "Towards the Synthesis of Epothilone A: Enantioselective Preparation of the Thiazole Sidechain and Macrocyclic Ring Closure", *Tetrahedron Lett.*, vol. 38, No. 12, 2061-2064 (1997).

Schinzer, D., et al., "Syntheses of (–)-Epothilone A", *Chem. Eur. J.*, vol. 5, No. 9, 2483-2491 (1999).

Schinzer, D., et al., "Syntheses of (–)-Epothilone B", *Chem. Eur. J.*, vol. 5, No. 9, 2492-2500 (1999).

Nicolaou, K. C., et al., "Synthesis and Biological Properties of C12,13-Cyclopropylepothilone A and Related Epothilones", *Chemistry & Biology*, vol. 5, No. 7, 365-372 (1998).

Altmann, K.H., et al., "Epothilones and Related Structures—A New Class of Microtubule Inhibitors With Patent In Vivo Antitumor Activity," Biochim. Biophys Acta, 1470 (2000).

Nicolaou et al., "Total Synthesis of Epothilone E and Analogs with Modified Side Chains Through The Stille Coupling Reaction", Angew. Chem. Int. Ed. 37, 84-87 (1998).

Nicolaou et al., "Total Synthesis of Oxazole- and Cyclopropane-Containing Epothilone B Analogues by the Macrolactonization Approach", Chemistry, European Journal, vol. 3, No. 12, 1971-1986 (1997).

Nicolaou et al., "Chemical Biology of Epothilones", Angew. Chem. Int. Ed., 37, 2014-2045 (1988).

\* cited by examiner

PHARMACEUTICAL COMPOSITIONS AND METHODS OF USING C-21 MODIFIED EPOTHILONE DERIVATIVES

CROSS-REFERENCE TO RELATED APPLICATION

This application claims the benefit of U.S. Provisional Application No. 60/380,634, filed May 15, 2002, incorporated herein by reference in its entirety.

FIELD OF THE INVENTION

The present invention relates generally to the field of cancer chemotherapy, pharmaceutical formulations and methods of administration of parenteral and oral compositions of certain epothilone analogs.

BACKGROUND OF THE INVENTION

Epothilones are macrocyclic lactones with useful antifungal and cytotoxic properties. Their action is based on stabilization of microtubules, causing mitotic arrest in rapidly dividing cells and thus inhibition of the growth of tumors. For reviews, see E. Nogales, *Ann. Rev. Biochem.*, 2000, 69:277–302; L. Wessjohann, *Angew. Chem. Int. Ed. Engl.* 1997, 36:715–718; Höfle et al., *Angew. Chem. Int. Ed. Engl.*, 1996, 35:1567–1569; and K. C. Nicolaou et al., *Angew. Chem. Intl. Ed. Engl.*, 1998, 37:2014–2045.

Among the numerous semi-synthetic derivatives of epothilone that have been reported, C-21 modified epothilones, and their derivatives, are particularly promising anti-tumor agents. C-21 modified epothilones are disclosed in U.S. Pat. No. 6,262,094; issued Jul. 17, 2000. The preparation of C-21 modified epothilones has been described by Höfle et al. in German applications DE 199 07 588 and DE 199 30 111, and in PCT international application WO 00/50423. Methods of preparing 21-amino epothilone derivatives are also described in U.S. provisional application Ser. No. 60/357,554; filed Feb. 15, 2002.

C-21 modified epothilones, however, are not readily compounded into suitable formulations for administration. They possess low solubility in water, degrade in contact with aqueous media, are sensitive to low pH when in solution, are light sensitive, are "Class D" cytotoxic and have poor wetting characteristics. Although one or two of these characteristics might be compensated for in compounding a pharmaceutical formulation for parenteral administration, the combination of all of these properties has until now presented a formidable challenge.

There remains a need for formulations of C-21 modified epothilone derivatives that are stable and easily prepared for administration in a safe and convenient manner. The present invention describes formulations whereby the epothilone analogs described above can be safely dispensed and administered via injection, without appreciable loss of potency.

Furthermore, many anti-cancer drugs have toxicity concerns. Indeed, the therapeutic profile of many potent antitumor drugs is poor as a result of toxicity. Therefore, there is also a need for methods of administration and dosing schedules that reduce or avoid the toxicity associated with antitumor agents. The methods can allow exploitation of potent antitumor agents that would otherwise not be used clinically.

BRIEF DESCRIPTION OF THE INVENTION

The present invention provides pharmaceutical compositions containing C-21 modified epothilones, and also provides methods for their preparation. It has been found that a suitable medium to form a solution of C-21 modified epothilones for lyophilization is an aqueous system, buffered to prevent degradation of the epothilone compounds.

It has been found that the stability of the C-21 modified epothilone derivatives can be significantly enhanced by carrying out the preparation of the lyophilization solution at a temperature below ambient. Unexpectedly, it has also been found that the properties of C-21 modified epothilone lyophiles are enhanced by the presence of dextran, and particularly by the presence of a combination of dextran and citric acid.

The lyophile of the C-21 modified epothilone derivatives may be reconstituted with Water for Injection, USP. Once reconstitution of the drug is achieved, the resulting solution may be further diluted with a suitable parenteral diluent prior to injection.

The present invention also encompasses a novel dosing schedule for C-21 modified epothilone compounds. In one embodiment, this schedule is useful in treating patients having solid tumors, particularly advanced solid tumors. Further, the methods of the invention can be used to treat and/or prevent metastatic as well as primary tumors. In another embodiment, the present invention encompasses the treatment of patients that have previously received either or both radiation therapy and chemotherapy for solid tumors. It has also been found that the C-21 modified epothilone compounds of the present invention, particularly the preferred compound, [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4,17-dioxabicyclo[14.1.0] heptadecane-5,9-dione, can be used to treat tumors refractory to radiation therapy or chemotherapy. The methods of the present invention are useful against cancer cells and, thus, tumors that are naturally insensitive or become insensitive to paclitaxel.

In one embodiment of the present invention, the dosing schedule comprises weekly administration of a C-21 modified epothilone compound of the invention, preferably as a one (1) hour infusion weekly on a continuous basis. In another embodiment, the administration is made weekly for a three week cycle. The dose range for weekly infusion is from 1 mg/m$^2$ to 100 mg/m$^2$, more preferably 1 mg/m$^2$ to 70 mg/m$^2$, even more preferably 10 mg/m$^2$ to 65 mg/m$^2$. In another embodiment, the dosing schedule includes both oral and intravenous administration of the same epothilone compound. For example, the weekly infusion can be followed or preceded by an oral administration of 10 mg/m$^2$ or greater, preferably 20 mg/m$^2$ or greater. In a specific embodiment, the administration regimen includes a three (3) week cycle of intravenous infusion once per week for about one (1) hour followed by or preceded by an oral dose administered one or more times in the week before the first intravenous administration of a cycle or the week after the last intravenous administration of a cycle. Other protocols are also encompassed within the present invention including, but not limited to:

(a) a daily dosing for 5 to 10 days followed by at least 3 days of no dosing;
(b) weekly dosing for two to ten weeks followed by at least one week of no dosing;
(c) dosing once every three weeks followed by at least one week of no dosing;

(d) a daily dosing for 3 days followed by at least 4 days of no dosing; and (e) a daily dosing of 5 days followed by at least 2 days of no dosing.

The present invention also contemplates the use of $H_1$ and $H_2$ antihistamines before, after and/or before and after a cycle of epothilone administration. Similarly, the invention encompasses the use of other chemotherapeutics, particularly anti-tumor agents, with epothilone cycle alone, or with the $H_1$ and $H_2$ blockers and the epohtilones of the invention.

In another embodiment of the present invention, the epothilone dosing schedule is used after the standard regiment for paclitaxel.

As discussed herein a wide variety of cancers are encompassed by the methods of the present invention. In a preferred embodiment, the methods of the invention are for the treatment of solid tumors including but not limited to breast, head and neck, sarcoma, colorectal, UPT, melanoma, esophagus, renal, cervix, thyroid, anal, ovarian, and colon.

The methods and compositions of the present invention describe formulations, preparation thereof and dosing regimen for epothilone analogs represented by formula I, formula Ia, formula Ib and formula Ic below:

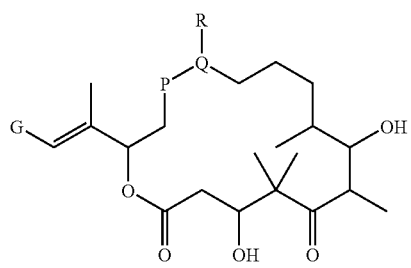

I wherein:
P-Q is a C,C double bond or an epoxide;
G is

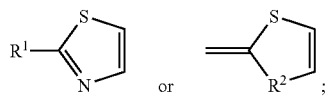

R is selected from the group of H, alkyl, and substituted alkyl;

$R^1$ is selected from the group consisting of

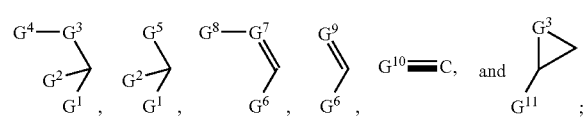

$R^2$ is

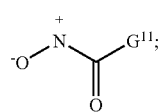

$G^1$ is selected from the group of H, halogen, CN, alkyl and substituted alkyl;

$G^2$ is selected from the group of H, alkyl, and substituted alkyl; p $G^3$ is selected from the group of O, S, and $NZ^1$;

$G^4$ is selected from the group of H, alkyl, substituted alkyl, $OZ^2$, $NZ^2Z^3$, $Z^2C=O$, $Z^4SO_2$, and optionally substituted glycosyl;

$G^5$ is selected from the group of halogen, $N_3$, NCS, SH, CN, NC, $N(Z^1)_3^+$ and heteroaryl;

$G^6$ is selected from the group of H, alkyl, substituted alkyl, $CF_3$, $OZ^5$, $SZ^5$, and $NZ^5Z^6$;

$G^7$ is $CZ^7$ or N;

$G^8$ is selected from the group of H, halogen, alkyl, substituted alkyl, $OZ^{10}$, $SZ^{10}$, $NZ^{10}Z^{11}$;

$G^9$ is selected from the group of O, S, —NH—NH— and —N=N—;

$G^{10}$ is N or $CZ^{12}$;

$G^{11}$ is selected from the group of $H_2N$, substituted $H_2N$, alkyl, substituted alkyl, aryl, and substituted aryl;

$Z^1$, $Z^6$, $Z^9$, and $Z^{11}$ are independently selected from the group H, alkyl, substituted alkyl, acyl, and substituted acyl;

$Z^2$ is selected from the group of H, alkyl, substituted alkyl, aryl, substituted aryl, and heterocycle;

$Z^3$, $Z^5$, $Z^8$, and $Z^{10}$ are independently selected from the group H, alkyl, substituted alkyl, acyl, substituted acyl, aryl, and substituted aryl;

$Z^4$ is selected from the group of alkyl, substituted alkyl, aryl, substituted aryl, and heterocycle;

$Z^7$ is selected from the group of H, halogen, alkyl, substituted alkyl, aryl, substituted aryl, $OZ^8$, $SZ^8$, and $NZ^8Z^9$; and $Z^{12}$ is selected from the group of H, halogen, alkyl, substituted alkyl, aryl, and substituted aryl;

with the proviso that when $R^1$ is

$G^1$, $G^2$, $G^3$ and $G^4$ cannot simultaneously have the following meanings:

$G^1$ and $G^2$=H, $G^3$=O and $G^4$=H or $Z^2C$=O where $Z^2$=alkyl group, and with the proviso that when $R^1$ is

$G^1$, $G^2$ or $G^5$ cannot simultaneously have the following meanings: $G^1$ and $G^2$=H, and $G^5$=F;

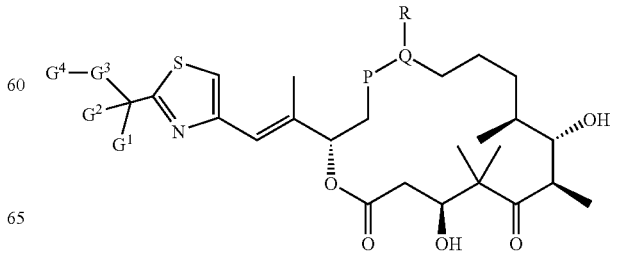

Ia wherein:

P-Q is a C,C double bond or an epoxide,

R is a H atom or a methyl group, $G^1$ is an H atom, an alkyl group, a substituted alkyl group or a halogen atom, $G^2$ is an H atom, an alkyl group or a substituted alkyl group, $G^3$ is an O atom, an S atom or an $NZ^1$ group with $Z^1$ being an H atom, an alkyl group, a substituted alkyl group, an acyl group, or a substituted acyl group, and $G^4$ is an H atom, an alkyl group, a substituted alkyl group, an $OZ^2$ group, an $NZ^2Z^3$ group, a $Z^2C=O$ group, a $Z^4SO_2$ group or an optionally substituted glycosyl group with $Z^2$ being a H atom, an alkyl group, a substituted alkyl group, an aryl group, a substituted aryl group or a heterocyclic group, $Z^3$ an H atom, an alkyl group, a substituted alkyl group, an acyl group or a substituted acyl group, and $Z^4$ an alkyl, a substituted alkyl, an aryl, a substituted aryl or a heterocyclic group, with the proviso that $G^1$, $G^2$, $G^3$ and $G^4$ cannot have simultaneously the following meanings: $G^1$ and $G^2$=H atom, $G^3$=O atom and $G^4$=H atom or $Z^2C=O$ with $Z^2$=alkyl group;

Ib

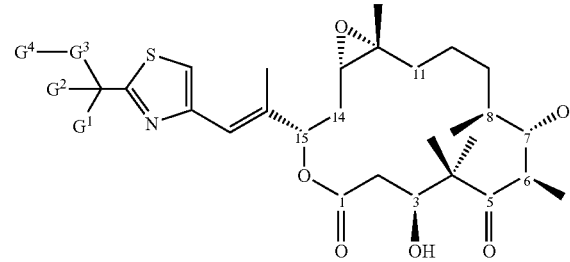

wherein $G^1$, $G^2$, $G^3$, $G^4$, $Z^1$, $Z^2$ and $Z^3$ are as defined above; and Ic

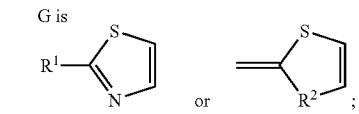

I wherein:

P-Q is a C,C double bond or an epoxide;

G is

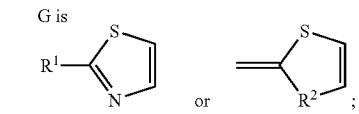

or

R is selected from the group of H, alkyl, and substituted alkyl;

$R^1$ is selected from the group consisting of $G^4$—$G^3$, $G^5$, $G^8$—$G^7$, $G^9$, $G^{10}\!=\!C$, and $G^{11}$ ;
$G^2$  $G^2$       $G^6$  $G^6$
$G^1$  $G^1$ $R^2$ is $G^1$ is selected from the group of H, halogen, CN, alkyl and substituted alkyl;

$G^2$ is selected from the group of H, alkyl, and substituted alkyl;

$G^3$ is selected from the group of O, S, and $NZ^1$;

$G^4$ is selected from the group of H, alkyl, substituted alkyl, $OZ^2$, $NZ^2Z^3$, $Z^2C=O$, $Z^4SO_2$, and optionally substituted glycosyl;

$G^5$ is selected from the group of halogen, $N_3$, NCS, SH, CN, NC, $N(Z^1)_3^+$ and heteroaryl;

$G^6$ is selected from the group of H, alkyl, substituted alkyl, $CF_3$, $OZ^5$, $SZ^5$, and $NZ^5Z^6$;

$G^7$ is $CZ^7$ or N;

$G^8$ is selected from the group of H, halogen, alkyl, substituted alkyl, $OZ^{10}$, $SZ^{10}$, $NZ^{10}Z^{11}$;

$G^9$ is selected from the group of O, S, —NH—NH— and —N=N—;

$G^{10}$ is N or $CZ^{12}$;

$G^{11}$ is selected from the group of $H_2N$, substituted $H_2N$, alkyl, substituted alkyl, aryl, and substituted aryl;

$Z^1$, $Z^6$, $Z^9$, and $Z^{11}$ are independently selected from the group H, alkyl, substituted alkyl, acyl, and substituted acyl;

$Z^2$ is selected from the group of H, alkyl, substituted alkyl, aryl, substituted aryl, and heterocycle;

$Z^3$, $Z^5$, $Z^8$, and $Z^{10}$ are independently selected from the group H, alkyl, substituted alkyl, acyl, substituted acyl, aryl, and substituted aryl;

DETAILED DESCRIPTION OF THE INVENTION

The present invention provides pharmaceutical compositions containing C-21 modified epothilone derivatives of general formula I:

$Z^4$ is selected from the group of alkyl, substituted alkyl, aryl, substituted aryl, and heterocycle;

$Z^7$ is selected from the group of H, halogen, alkyl, substituted alkyl, aryl, substituted aryl, $OZ^8$, $SZ^8$, and $NZ^8Z^9$; and $Z^{12}$ is selected from the group of H, halogen, alkyl, substituted alkyl, aryl, and substituted aryl;

with the proviso that when $R^1$ is

$G^1$, $G^2$, $G^3$ and $G^4$ cannot simultaneously have the following meanings:

$G^1$ and $G^2$=H, $G^3$=O and $G^4$=H or $Z^2C$=O where $Z^2$=alkyl group, and with the proviso that when $R^1$ is

$G^1$, $G^2$ or $G^5$ cannot simultaneously have the following meanings: $G^1$ and $G^2$=H, and $G^5$=F.

Where P-Q is a carbon-carbon double bond, the 12,13-olefin may be of E or Z stereochemistry. In a preferred embodiment, the pharmaceutical composition of the present invention comprises a compound of formula I wherein P-Q is an epoxide.

Formula Ia provides another example of a C-21 modified epothilone compound suitable for use in the methods and compositions of the present invention:

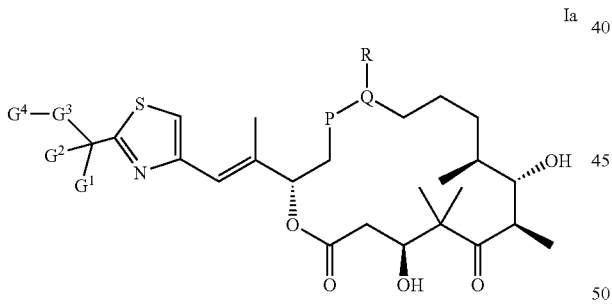

wherein:

P-Q is a C,C double bond or an epoxide,

R is a H atom or a methyl group, $G^1$ is an H atom, an alkyl group, a substituted alkyl group or a halogen atom, $G^2$ is an H atom, an alkyl group or a substituted alkyl group, $G^3$ is an O atom, an S atom or an $NZ^1$ group with $Z^1$ being an H atom, an alkyl group, a substituted alkyl group, an acyl group, or a substituted acyl group;

$G^4$ is an H atom, an alkyl group, a substituted alkyl group, an $OZ^2$ group, an $NZ^2Z^3$ group, a $Z^2C$=O group, a $Z^4SO_2$ group or an optionally substituted glycosyl group with $Z^2$ being a H atom, an alkyl group, a substituted alkyl group, an aryl group, a substituted aryl group or a heterocyclic group;

$Z^3$ an H atom, an alkyl group, a substituted alkyl group, an acyl group or a substituted acyl group; and $Z^4$ an alkyl, a substituted alkyl, an aryl, a substituted aryl or a heterocyclic group;

with the proviso that $G^6$, $G^2$, $G^3$ and $G^4$ cannot simultaneously have the following meanings: $G^1$ and $G^2$=H atom, $G^3$=O atom and $G^4$=H atom or $Z^2C$=O with $Z^2$=alkyl group.

A preferred compound of formula Ia is the compound of formula Ib:

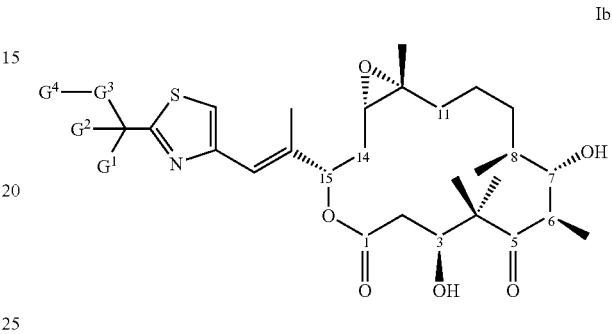

wherein $G^1$, $G^2$, $G^3$, $G^4$, $Z^1$, $Z^2$ and $Z^3$ are as defined above.

In another preferred embodiment, the compound of formula I is the compound of formula Ic shown below, which is

[1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4,17-dioxabicyclo[14.1.0]heptadecane-5,9-dione (Compound A).

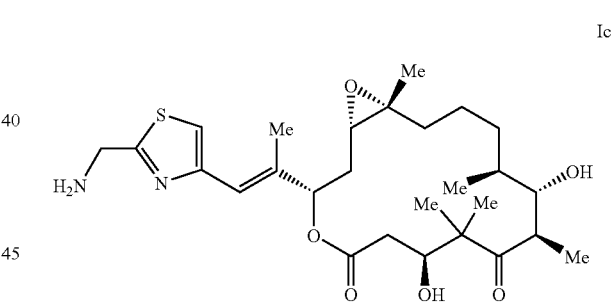

DEFINITIONS

Listed below are definitions of various terms used to describe this invention. These definitions apply to the terms as they are used throughout this specification, unless otherwise indicated in specific instances.

As used herein, the term "alkyl" refers to straight or branched chain optionally substituted hydrocarbon groups of 1 to 20 carbon atoms, preferably 1 to 7 carbon atoms. The term "lower alkyl" refers to optionally substituted alkyl groups having from 1 to about 7 carbon atoms, preferably 1 to about 4 carbon atoms.

As used herein, the term "substituted alkyl" refers to an alkyl group substituted by, for example, one to four substituents, such as, halo, trifluoromethyl, trifluoromethoxy, hydroxy, alkoxy, cycloalkyoxy, heterocylooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. $SO_2NH_2$), substituted sulfonamido, nitro, cyano, carboxy, carbamyl (e.g. $CONH_2$), substituted carbamyl (e.g. CONH alkyl, CONH aryl, CONH aralkyl or cases where there are two substituents on the nitrogen selected from alkyl, aryl or aralkyl), alkoxycarbonyl, aryl, substituted aryl, guanidino and heterocyclos, such as, indolyl, imidazolyl, furyl, thienyl, thiazolyl, pyrrolidyl, pyridyl, and pyrimidyl. Where noted above where the substituent is further substituted it will be with halogen, alkyl, alkoxy, aryl or aralkyl.

As used herein, the term "halogen" or "halo" refers to fluorine, chlorine, bromine and iodine.

As used herein, the term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

As used herein, the term "aralkyl" refers to an aryl group bonded directly through an alkyl group, such as benzyl.

As used herein, the term "substituted aryl" refers to an aryl group substituted by, for example, one to four substituents such as alkyl; substituted alkyl, phenyl, substituted phenyl, heterocyclo, halo, trifluoromethoxy, trifluoromethyl, hydroxy, alkoxy, cycloalkyloxy, heterocyclooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, and aryloxy. The substituent may be further substituted by halo, hydroxy, alkyl, alkoxy, aryl, substituted aryl, substituted alkyl or aralkyl.

As used herein, the term "cycloalkyl" refers to optionally substituted, saturated cyclic hydrocarbon ring systems, preferably containing 1 to 3 rings and 3 to 7 carbons per ring which may be further fused with an unsaturated C3–C7 carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

As used herein, the terms "heterocycle", "heterocyclic" and "heterocyclo" refer to an optionally substituted, fully saturated or unsaturated, aromatic or nonaromatic cyclic group, for example, a 4 to 15 membered system or a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include, but are not limited to, pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1,1-dioxothienyl, dioxanyl, isothiazolidinyl, thietanyl, thiiranyl, triazinyl, and triazolyl.

Exemplary bicyclic heterocyclic groups include, but are not limited to, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3, 1-b]pyridinyl or furo[2, 3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, and thienothienyl.

Exemplary substituents for the terms "heterocycle," "heterocyclic," "heterocyclo," "monocyclic heterocyclic" and "bicyclic heterocyclic" include, but are not limited to, one or more substituent groups as described above for substituted alkyl or substituted aryl, and smaller heterocycles, such as, epoxides, aziridines and the like.

As used herein, the term "heteroatoms" shall include oxygen, sulfur and nitrogen.

As used herein, the prefix "lower" stands for a moiety having up to and including 7 carbon atoms, preferably up to and including 4 carbon atoms.

As used herein, the term "bioavailable" means the extent to which a drug is absorbed into a living system and made available in the circulating blood of the living system. Methods to determine the bioavailability of drugs are well known to those of ordinary skill in the art.

As used herein, the phrase "sufficiently bioavailable to have a pharmacological effect" means that the epothilones are greater than 20 percent bioavailable, preferably greater than 30 percent bioavailable, and more preferably greater than 50 percent bioavailable.

As used herein, the term "pharmaceutically acceptable salt" refers to a salt prepared from an epothilone of Formula I, Ia, Ib or Ic having a basic functional group, such as an amine, with a pharmaceutically acceptable non-toxic inorganic or organic acid. Suitable non-toxic acids include, but are not limited to, acetic, benzenesulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acids. Salts formed with acids can be obtained, for example, with an epothilone of Formula I, Ia, Ib or Ic having a basic functional group and an equivalent amount of a non-toxic acid to provide an acid addition salt. The reaction is typically carried out in a medium in which the acid addition salt precipitates or an aqueous medium followed by evaporation. The term "pharmaceutically acceptable salt" also refers to a salt prepared from an epothilone of Formula I, Ia, Ib or Ic having an acidic functional group, such as a carboxylic acid functional group, and a pharmaceutically acceptable non-toxic inorganic or organic base. Suitable non-toxic bases include hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N,-dimethyl-N-(2-hydroxyethyl)amine, or tri-(2-hydroxyethyl)amine; N-methyl-D-glucamine; and amino acids such as arginine, lysine, and the like. Salts formed with bases can be obtained, for example, with an epothilone of Formula I, Ia, Ib or Ic having an acidic functional group and an equivalent amount of a non-toxic base. The reaction is typically carried out in a medium in which the salt precipitates or an aqueous medium followed by evaporation.

The invention also includes zwitterions.

As used herein, the term "pharmaceutically acceptable acid neutralizing buffer" refers to a combination of a pharmaceutically acceptable non-toxic acid and a pharmaceutically acceptable non-toxic salt of an acid that when added to a solution provides a solution that is more resistant to change of pH, compared to a solution without the buffer, when acid or alkali is added to the solution. The term "pharmaceutically acceptable acid neutralizing buffer" also includes compounds, such as basic compounds, that when added to an acidic solution neutralizes the acid and increases the pH of the solution.

As used herein, the term "clathrate" means an inclusion compound formed by the envelopment of a molecule of a "guest" compound in a cage-like hollow space formed by combination of several molecules of a "host" compound.

As used herein, the term "pro-drug" means a derivative of a compound that can hydrolyze, oxidize, or otherwise react under biological conditions (in vitro or in vivo) to provide an epothilone compound of formula I, Ia, Ib or Ic. For example, carboxylic esters are conveniently formed by esterifying carboxylic acid functionalities; if the epothilone of formula I, Ia, Ib or Ic includes an acid functional group it can be esterified to provide a pro-drug. Various pro-drugs are well known in the art. (For examples of pro-drugs, see: Design of Prodrugs, edited by H. Bundgaard, Elsevier, 1985; Methods in Enzymology, vol. 42, p. 309–396, edited by K. Widder et al., Academic Press, 1985; A Textbook of Drug Design and Development, edited by Krosgaard-Larsen and H, Bundgaard, chapter 5, "Design and Application of Prodrugs," by H. Bundgaard, p. 113–191, 1991; H. Bundgaard, "Advanced Drug Delivery Reviews," 8, 1–38, 1992; H. Bundgaard et al., Journal of Pharmaceutical Sciences, 77, 285, 1988; and N. Kakeya et al., Chem. Phar. Bull., 32, 692, 1984).

UTILITY AND USES OF C-21 MODIFIED EPOTHILONES OR COMPOSITIONS THEREOF

Any epothilone of formula I, formula Ia, formula Ib or formula Ic can be used in the methods and compositions of the present invention. Preferably, the epothilones are soluble in water. Epothilones of formula I can be prepared by the methods disclosed in U.S. Pat. No. 6,262,094, issued Jul. 17, 2001, the contents of which are expressly incorporated herein by reference. One of ordinary skill in the art would also recognize that epothilones of formula I, Ia, Ib and Ic could also be prepared by suitable modification of the methodologies disclosed in, for example, K. C. Nicolaou et al., "An Approach to Epothilones Based on Olefin Metathesis," Angew. Chem Int. Ed. Engl., 35(20): 2399–2401 (1996); K. C. Nicolaou et al., "The Total Synthesis of Epothilone A: The Macrolactonization Approach," Angew. Chem Int. Ed. Engl., 36(5): 525–527 (1997); K. C. Nicolaou et al., "Designed Epothilones: Combinatorial Synthesis, Tubulin Assembly Properties, and Cytoxic Action Against Taxol Resistant Tumor Cells," Angew. Chem Int. Ed. Engl., 36(19): 2097–2103 (1997); K. C. Nicolaou et al., "The Olefin Metathesis Approach to Epothilone A and its Analogues", J. Am. Chem. Soc., 119(34): 7960–7973 (1997); K. C. Nicolaou et al., "Total Syntheses of Epothilones A and B via a Macrolactonization-Based Strategy," J. Am. Chem. Soc., 119(34): 7974–7991 (1997); K. C. Nicolaou et al., "Synthesis of Epothilones A and B in Solid and Solution Phase," Nature, 387: 268–272 (1997); and D. Meng et al., "Remote Effects in Macrolide Formation Through Ring-Forming Olefin Metathesis: An Application to the Synthesis of Fully Active Epothilone Congeners," J. Am. Chem. Soc., Vol. 119, No. 11, 2733–2734 (1997).

Preferably, the epothilones are crystalline and anhydrous. Optionally, the epothilones are sterilized before being used in the compositions of the invention.

UTILITY AND USES OF THE EPOTHILONES OR COMPOSITIONS THEREOF

The epothilones of the invention are microtubule-stabilizing agents and, thus, can be used to treat a variety of cancer or other diseases of abnormal cell proliferation. The methods of the invention are particularly useful for administering one or more epothilones of formula I, Ia, Ib or Ic, or a pharmaceutically acceptable salt, solvate, clathrate, hydrate, or prodrug thereof, to a patient suffering from cancer or other hyperproliferative cellular disease. As used herein, the term "cancer" includes, but is not limited to, solid tumors and blood born tumors. The term cancer refers to disease of skin, tissues, organs, bone, cartilage, blood and vessels. The term "cancer" further encompasses primary and metastatic cancers.

Examples of cancers that can be treated with the methods of the invention include, but are not limited to, carcinoma, including that of the bladder, breast, colon, kidney, lung, ovary, pancreas, stomach, cervix, thyroid, and skin, including squamous cell carcinoma; hematopoietic tumors of lymphoid lineage, including, but not limited to, leukemia, acute lymphocytic leukemia, acute lymphoblastic leukemia, B-cell lymphoma, T-cell lymphoma, Hodgkins lymphoma, non-Hodgkins lymphoma, hairy cell lymphoma, and Burketts lymphoma; hematopoietic tumors of myeloid lineage including, but not limited to, acute and chronic myelogenous leukemias and promyelocytic leukemia; tumors of mesenchymal origin including, but not limited to, fibrosarcoma, rhabdomyosarcoma, and osteosarcoma; other tumors including melanoma, seminoma, tetratocarcinoma, neuroblastoma, and glioma; tumors of the central and peripheral nervous system including, but not limited to, astrocytoma, neuroblastoma, glioma, and schwannomas; and other tumors including, but not limited to, xenoderma, pigmentosum, keratoactanthoma, thyroid follicular cancer, and teratocarcinoma.

The compositions and methods of the present invention comprising C-21 modified epothilones of formula I, formula Ia, formula Ib or formula Ic are useful for treating patients who have been previously treated for cancer, as well as those who have not previously been treated for cancer. Indeed, the methods and compositions of this invention can be used in first-line and second-line cancer treatments. Furthermore, compositions and methods comprising these epothilones are useful for treating refractory cancers.

Furthermore, compounds of formula I, Ia, Ib or Ic may be administered in combination with radiation, or other anti-cancer and/or cytotoxic agents and treatments useful in the treatment of cancer or other proliferative diseases. Especially useful are anti-cancer and cytotoxic drug combinations wherein the second drug chosen acts in a different manner or different phase of the cell cycle, e.g., S phase, than the present compounds of formula I, Ia, Ib and Ic, which exert their effects at the $G_2$-M phase.

Example classes of anti-cancer and cytotoxic agents include, but are not limited to, alkylating agents, such as nitorgen mustards, alkyl sulfonates, nitrosoureas, ethylenimines, and triazenes; antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids, estrogens/antiestrogens, androgens/antiandrogens, progestins, and luteinizing hormone-releasing hormone anatagonists, octreotide acetate; microtubule-disruptor agents, such as ecteinascidins or their analogs and derivatives; microtubule-stabilizing agents such as paclitaxel (Taxol®), docetaxel (Taxotere®); plant-derived products, such as vinca alkaloids, epipodophyllotoxins, taxanes; and topoisomerase inhibitors; prenyl-protein transferase inhibitors; and miscellaneous agents such as, hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators, and monoclonal antibodies. Compounds represented by formulae I and II may also be used in conjunction with radiation therapy.

Representative examples of these classes of anti-cancer and cytotoxic agents include, but are not limited to, mechlorethamine hydrochlordie, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Some preferred members of these classes include, but are not limited to, paclitaxel, cisplatin, carboplatin, doxorubicin, carminomycin, daunorubicin, aminopterin, methotrexate, methopterin, mitomycin C, ecteinascidin 743, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine, and leurosine.

Examples of anti-cancer and other cytotoxic agents include the following: cyclin dependent kinase inhibitors as found in WO 99/24416; and prenyl-protein transferase inhibitors as found in WO 97/30992 and WO 98/54966.

The compounds may also be administered with or after anti-cancer and cytotoxic agents that are neurotoxic, i.e., poisonous to the nervous system.

Without being bound by any theory regarding mechanism or morphology, the compounds represented by formulae I and II may also be used to treat conditions other than cancer or other proliferative diseases. Such conditions include, but are not limited to viral infections such as herpesvirus, poxvirus, Epstein-Barr virus, Sindbis virus and adenovirus; autoimmune diseases such as systemic lupus erythematosus, immune mediated glomerulonephritis, rheumatoid arthritis, psoriasis, inflammatory bowel diseases and autoimmune diabetes mellitus; neurodegenerative disorders such as Alzheimer's disease, AIDS-related dementia, Parkinson's disease, amyotrophic lateral sclerosis, retinitis pigmentosa, spinal muscular atrophy and cerebellar degeneration; AIDS; myelodysplastic syndromes; aplastic anemia; ischemic injury associated myocardial infarctions; stroke and reperfusion injury; restenosis; arrhythmia; atherosclerosis; toxin-induced or alcohol induced liver diseases; hematological diseases such as chronic anemia and aplastic anemia; degenerative diseases of the musculoskeletal system such as osteoporosis and arthritis; aspirin-sensitive rhinosinusitis; cystic fibrosis; multiple sclerosis; kidney diseases; and cancer pain.

Epothilones of formula I, Ia, Ib and Ic may also inhibit tumor angiogenesis, thereby affecting abnormal cellular proliferation. Accordingly, the methods of the invention may also be useful in treating certain forms of blindness related to retinal vascularization, arthritis, especially inflammatory arthritis, multiple sclerosis, restinosis, and psoriasis.

Epothilones of formula I, Ia, Ib and Ic may also induce or inhibit apoptosis, a physiological cell death process critical for normal development and homeostasis. Alterations of apoptotic pathways contribute to the pathogenesis of a variety of human diseases. Accordingly, the methods of the invention will be useful in the treatment of a variety of human diseases with aberrations in apoptosis including cancer (particularly, but not limited to, follicular lymphomas, carcinomas with p53 mutations, hormone dependent tumors of the breast, prostrate and ovary, and precancerous lesions such as familial adenomatous polyposis), viral infections (including, but not limited to, herpesvirus, poxvirus, Epstein-Barr virus, Sindbis virus and adenovirus), autoimmune diseases (including, but not limited to, systemic lupus erythematosus, immune mediated glomerulonephritis, rheumatoid arthritis, psoriasis, inflammatory bowel diseases and autoimmune diabetes mellitus), neurodegenerative disorders (including, but not limited to, Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including but not limited to chronic anemia and aplastic anemia), degenerative diseases of the musculoskeletal system (including, but not limited to, osteoporosis and arthritis), aspirin-sensitive rhinosinusitis, cystic fibrosis, multiple sclerosis, kidney diseases, and cancer pain.

Epothilones of formula I, Ia, Ib and Ic may also be formulated or co-administered with other therapeutic agents that are selected for their particular usefulness in administering therapies associates with the aforementioned conditions. For example, each of the compounds of formula I, Ia, Ib and Ic may be formulated with agents to prevent nausea, hypersensitivity, and gastric irritation, such as anti-emetics, and $H_1$ and $H_2$ antihistamines. The above therapeutic agents, when employed in combination with an epothilone of formula I, Ia, Ib or Ic, may be used in those amounts indicated in the Physicians' Desk Reference (PDR) or as otherwise determined by one of ordinary skill in the art.

Epothilones of formula I, Ia, Ib and Ic may be administered orally or intravenously. Buffers of the methods of the present invention function to temporarily neutralize gastric fluid and thereby reduce degradation of the epothilone in the stomach of the patient. In addition, in aqueous and partially aqueous liquid oral formulations comprising one or more epothilones of Formula I, Ia, Ib or Ic, or a pharmaceutically acceptable salt, solvate, clathrate, hydrate, or prodrug thereof, the buffer reduces decomposition of the epothilone of Formula I, Ia, Ib or Ic. Applicants have surprisingly discovered that liquid oral dosage forms comprising one or more epothilones of Formula I, Ia, Ib or Ic, or a pharmaceutically acceptable salt, solvate, clathrate, hydrate, or prodrug thereof, and a buffer are more stable than a liquid oral dosage form without a buffer.

Buffers useful in the methods and compositions of the present invention may be readily prepared by combining one or more acids and the salt of one or more acids in a ratio such that the combination, when dissolved in an aqueous solution, provides a solution having a pH of between about 5 and 9. Typically, the one or more acids will have a pKa of between about 4 and 10. One of ordinary skill in the art would readily recognize how to prepare buffers that provide a solution having the desired pH value. In addition, the invention contemplates use of buffer compounds, such as basic compounds, that when added to an acidic solution increase the pH of the solution.

As discussed above, epothilones of formula I, Ia, Ib or Ic may be administered orally or intravenously (parenterally). It should be recognized that when epothilones of the present invention are administered parenterally, it avoids the gastrointestinal system and overcome any bioavailability concerns. However, in some instances such administration may be inconvenient and uncomfortable for the patient and provides other potential adverse effects. The compositions of this invention and the methods enable the oral route of administration to be used which is a significant advantage, particularly for human patients.

Administering one or more epothilones of formula I, Ia, Ib or Ic, or a pharmaceutically acceptable salt, solvate, clathrate, hydrate, or prodrug thereof, in combination with a pharmaceutically acceptable acid neutralizing buffer provides increased bioavailability of the one or more epothilones of formula I, Ia, Ib or Ic. Without being limited by theory, it is believed that the increased bioavailability is due, at least in significant part, to the buffer decreasing the rate of decomposition of the epothilones of formula I, Ia, Ib or Ic, or a pharmaceutically acceptable salt, solvate, clathrate, hydrate, or prodrug thereof, in the acidic environment of the stomach. Certain epothilones, including the epothilone of formula Ic, are unstable in acidic aqueous environments and decompose, presumably by an acid catalyzed hydrolytic opening of the epoxide ring. For example, the time for 5% drug loss ($t_{95}$) at 37° C. for an aqueous solution of Compound A (epothilone of formula Ic) is approximately 14 h at pH 7, but <0.2 hours at pH 2.5. Thus, when epothilones of formula I, Ia, Ib or Ic, or a pharmaceutically acceptable salt, solvate, clathrate, hydrate, or prodrug thereof, are orally administered they decompose in the stomach of the patient such that they are either minimally absorbed or not absorbed by the gastrointestinal tract.

When one or more epothilones of formula I, Ia, Ib or Ic, or a pharmaceutically acceptable salt, solvate, clathrate, hydrate, or prodrug thereof, are administered to a patient in combination with a pharmaceutically acceptable acid neutralizing buffer, however, the buffer neutralizes acid in the stomach of the patient so that the rate of decomposition of the one or more epothilones of formula I, Ia, Ib or Ic, or a pharmaceutically acceptable salt, solvate, clathrate, hydrate, or prodrug thereof is sufficiently decreased so that the one or more epothilones of formula I, Ia, Ib or Ic, or a pharmaceutically acceptable salt, solvate, clathrate, hydrate, or prodrug thereof remain in the gastrointestinal tract for sufficient time to be absorbed.

In another embodiment of the present invention an antiacid such as hydroxides of aluminum and magnesium; carbonates, such as sodium carbonate and calcium carbonate; silicates; and phosphates can be used to neutralize the acid in the stomach before during or after epothilone administration.

When orally administered according to the methods of the invention, the epothilones of formula I, Ia, Ib or Ic, or a pharmaceutically acceptable salt, solvate, clathrate, hydrate, or prodrug thereof are at least about 20% bioavailable. For example, these epothilones may be at least about 40% bioavailable. As another example, these epothilones may be at least about 50% bioavailable.

In one embodiment of the invention, the one or more epothilones of formula I, Ia, Ib or Ic, or a pharmaceutically acceptable salt, solvate, clathrate, hydrate, or prodrug thereof and the pharmaceutically acceptable acid neutralizing buffer are provided in a single oral dosage form and are administered simultaneously. The single composition comprising the combination of one or more epothilones of formula I, Ia, Ib or Ic, or a pharmaceutically acceptable salt, solvate, clathrate, hydrate, or prodrug thereof, and the pharmaceutically acceptable acid neutralizing buffer may be administered as a solid oral dosage form (e.g., a tablet, capsule, or powder) or a liquid oral dosage form (e.g., a solution, suspension, or elixir). The solution or suspension can be constituted just prior to administration using the appropriate solvents or cosolvents to dissolve the epothilone and the buffer components.

For example, the one or more epothilones of formula I, Ia, Ib or Ic, or a pharmaceutically acceptable salt, solvate, clathrate, hydrate, or prodrug thereof, and the pharmaceutically acceptable acid neutralizing buffer may be administered simultaneously as a solution of the epothilone of formula I, Ia, Ib or Ic dissolved in a liquid comprising propylene glycol:ethanol:phosphate buffer (for example at 1M, about pH 8) in a ratio of about 58:12:30, respectively.

In another embodiment of the invention, the epothilone of formula I, Ia, Ib or Ic and the pharmaceutically acceptable acid neutralizing buffer are provided as separate distinct pharmaceutical compositions and are administered separately. Each of which are administered as a solid oral dosage form or a liquid oral dosage form.

When the one or more epothilones of formula I, Ia, Ib or Ic, or a pharmaceutically acceptable salt, solvate, clathrate, hydrate, or prodrug thereof and the pharmaceutically acceptable acid neutralizing buffer are administered separately, the pharmaceutically acceptable acid neutralizing buffer may be orally administered before, after, or both before and after the desired epothilone of formula I, Ia, Ib or Ic is administered. For example, the pharmaceutically acceptable acid neutralizing buffer is administered both before and after oral administration of the desired epothilone of formula I, Ia, Ib or Ic, in an amount sufficient to neutralize the stomach acid.

When the pharmaceutically acceptable acid neutralizing buffer is administered before one or more epothilones of formula I, Ia, Ib or Ic, or a pharmaceutically acceptable salt, solvate, clathrate, hydrate, or prodrug thereof, it is administered within about 5 hours before administration of the epothilone. For example, the buffer is administered within about 3 hours before the epothilone. As another example, the buffer is administered within about 1 hour before the epothilone. In yet another example, the buffer is administered within about 10 minutes before the desired epothilone of formula I, Ia, Ib or Ic is administered. When the pharmaceutically acceptable acid neutralizing buffer is administered after the desired epothilone of formula I, Ia, Ib or Ic, or a pharmaceutically acceptable salt, solvate, clathrate, hydrate, or prodrug thereof, it is administered within about 5 hours after the epothilone. For example, the buffer is administered within about 3 hours after the epothilone. As another example, the buffer is administered within about 1 hour after the epothilone. As a further example, the buffer is administered within about 10 minutes after the desired epothilone of formula I, Ia, Ib or Ic is administered.

Pharmaceutical compositions and dosage forms suitable for oral administration can be presented as discrete dosage forms, such as, but not limited to, tablets (e.g., chewable tablets), caplets, capsules, powder in a sachet, enteric coated tablets, enteric coated beads, enteric coated soft gel capsules, and liquids (e.g., flavored syrups). Such dosage forms contain predetermined amounts of the active ingredient and may be prepared by methods of pharmacy well known to those skilled in the art (See *Remington's Pharmaceutical Sciences,* 18th ed., Mack Publishing, Easton Pa. (1990)).

In one embodiment, the epothilones of formula I, Ia, Ib or Ic, or a pharmaceutically acceptable salt, solvate, clathrate, hydrate, or prodrug thereof, are administered as an enteric coated pill or capsule to delay release of the epothilone until after the pharmaceutically effective acid neutralizing buffer is administered. Enteric coated tablets and capsules are capsules coated with a substances that resist solution in a gastric fluid but disintegrate in the intestine.

In one embodiment the buffer is administered as a dispersible tablet.

Typical oral dosage forms are prepared by combining the active ingredients in an intimate admixture with at least one excipient according to conventional pharmaceutical compounding techniques. Excipients can take a wide variety of forms depending on the form of preparation desired for administration. For example, excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents. Examples of excipients suitable for use in oral liquid dosage forms include, but are not limited to, water, glycols, oils, alcohols, flavoring agents, preservatives, and coloring agents.

Tablets and capsules represent convenient pharmaceutical compositions and oral dosage forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions and dosage forms of the invention is typically present in from about 50 to about 99 weight percent of the pharmaceutical composition or dosage form.

Disintegrants are used in the pharmaceutical compositions and dosage forms of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form the pharmaceutical compositions and solid oral dosage forms of the invention. The amount of disintegrant used varies based upon the type of formulation, and is readily discernible to those of ordinary skill in the art. Typical pharmaceutical compositions and dosage forms comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

The pharmaceutical compositions and dosage forms may further comprise one or more compounds that reduce the rate by which an active ingredient will decompose. Such compounds, which are referred to herein as "stabilizers," include, but are not limited to, antioxidants such as ascorbic acid and salt buffers.

Solutions for oral administration represent another convenient oral dosage form, in which case a solvent is employed. Liquid oral dosage forms are prepared by combining the active ingredient in a suitable solvent to form a solution, suspension, syrup, or elixir of the active ingredient in the liquid.

The solutions, suspensions, syrups, and elixirs may optionally comprise other additives including, but not limited to, glycerin, sorbitol, propylene glycol, sugars, flavoring agents, and stabilizers.

The magnitude of the therapeutic dose of the desired epothilone of formula I, Ia, Ib or Ic, or a pharmaceutically acceptable salt, solvate, clathrate, hydrate, or prodrug thereof, will typically vary with the specific disease and severity of the disease being treated. The dose, and perhaps the dose frequency, may also vary according to age, body weight, response, and the past medical history of the patient. Suitable dosing regimens can be readily selected by those skilled in the art with due consideration of such factors. Typically, the epothilone of formula I, Ia, Ib or Ic, or a pharmaceutically acceptable salt, solvate, clathrate, hydrate, or prodrug thereof, is orally administered in a total amount of about 0.01 to about 200 mg/kg/day. For example, the epothilone may be administered in a total amount of about 0.05 to about 50 mg/kg/day as a single dose or in divided doses such as from 1 to about 4 times per day. As another example, the compounds of formula I, Ia, Ib and Ic are administered in a dose less than about 100 mg/kg/day. For example, epothilones of formula I, Ia, Ib and Ic are administered in a dose less than 50 mg/kg/day in a single dose or in 1 to about 4 divided doses.

The invention encompasses pharmaceutical unit dosage forms of the desired epothilone comprising 5 mg/unit, 10 mg/unit, 15 mg/unit, 20 mg/unit, 25 mg/unit, 50 mg/unit, and 100 mg/unit. Similarly, liquid unit doses encompassed by the invention include, but are not limited to, 2.5 mg/mL and 10 mg/mL.

The term "total amount," as used herein, means the combined amount of the epothilones of Formula I, Ia, Ib or Ic, or a pharmaceutically acceptable salt, solvate, clathrate, hydrate, or prodrug thereof, if more than one epothilone of Formula I, Ia, Ib or Ic, or a pharmaceutically acceptable salt, solvate, clathrate, hydrate, or prodrug thereof is in a unit dosage form or administered to the patient.

Further, the pharmaceutically acceptable acid neutralizing buffer is administered in an amount sufficient to deliver at least about 20 milliequivalents of acid neutralization capacity. For example, the pharmaceutically acceptable acid neutralizing buffer is administered in an amount sufficient to deliver at least about 30 milliequivalents of acid neutralization capacity, at least about 40 milliequivalents of acid neutralization capacity, or at least about 50 milliequivalents of acid neutralization capacity.

The invention also encompasses pharmaceutical unit dosage forms of the desired buffer comprising about 1 to about 200 mg/unit, such as, for example, about 5 to about 100 mg/unit, or about 5 to about 50 mg/unit. Similarly, liquid unit doses of the buffer encompassed by the invention include about 1 to 200 mg/unit, such as, for example, about 5 to 100 mg/unit, or about 5 to 50 mg/unit, dissolved in about 50 mL to 300 mL of a solvent, such as about 100 mL to 200 mL of a solvent or about 110 mL to 150 mL of a solvent.

Typically, the pharmaceutically acceptable acid neutralizing buffer is administered as an aqueous solution having a pH of between about 5 to about 9. For example, the pharmaceutically acceptable acid neutralizing buffer is administered as an aqueous solution having a pH of between about 6 to about 8.5 or about 7 to about 8. Any pharmaceutically acceptable acid neutralizing buffer that provides a solution having a pH in the desired range may be used in the methods of the invention. As an eample, the pharmaceutically acceptable acid neutralizing buffer may be a dibasic phosphate-monobasic phosphate buffer or a dibasic phosphate buffer-citric acid-citrate buffer.

In one embodiment of the invention, the patient is first administered the pharmaceutically acceptable acid neutralizing buffer as about 150 mL of an aqueous solution comprising anhydrous dibasic sodium phosphate (about 0.2 M), sodium citrate dihydrate (about 0.07 M), and anhydrous citric acid (about 0.008 M) at a pH of about 7.4; followed by oral administration of one or more epothilones of Formula I, Ia, Ib or Ic, or a pharmaceutically acceptable salt, solvate, clathrate, hydrate, or prodrug thereof as a liquid dosage form, for example, in a propylene glycol:ethanol system having a ratio of about 80:20, or in an aqueous or nonaqueous suspension, or as an aqueous or nonaqueous solution; followed by oral administration of another about 150 mL aqueous solution comprising anhydrous dibasic sodium phosphate (about 0.2 M), sodium citrate dihydrate (about 0.07 M), and anhydrous citric acid (about 0.008 M) at a pH of about 7.4. The pharmaceutically acceptable acid neutralizing buffer could also be administered as a solid dosage form. Buffer or water, or both, could be administered following administration of the epothilone compounds of formula I, Ia, Ib or Ic, in a volume of, for example, about at least 150 mL to aid in rinsing the epothilone liquid formulation through the upper gastrointestinal (g.i.) tract (i.e., mouth, esophagus, stomach) and into the small intestine where the pH is more favorable.

Those skilled in the art would readily recognize a variety of buffers that could be used in the methods, compositions, and dosage forms of the invention. Typical buffers include, but are not limited to, pharmaceutically acceptable weak acids, weak bases, or mixtures thereof. For example, the buffer components are water soluble materials such as phosphoric acid, tartaric acids, lactic acid, succinic acid, citric acid, acetic acid, ascorbic acid, aspartic acid, glutamic acid, and salts thereof. The pharmaceutically acceptable acid neutralizing buffer may be a dibasic phosphate-monobasic phosphate buffer, a dibasic phosphate buffer-citric acid-citrate buffer, or buffers of aluminum, magnesium, calcium, borate, carbonate and/or TRIS salts. These buffers are commercially available or can be readily prepared by one of ordinary skill in the art using commercially available buffering agents such as those mentioned above.

The present invention is based on the discovery that the stability of C-21 modified epothilone derivatives can be significantly enhanced by the presence of a combination of a dibasic carboxylic acid and a dextran polymer. For example, the dibasic acid may be citric acid or succinic acid, and the dextran polymer has an average molecular weight of about 40,000 (e.g., dextran 40). Preparation of a solution containing a C-21 modified epothilone derivative, a dibasic carboxylic acid and a dextran polymer can be carried out at a temperature below ambient, for example, from about 3° C. to about 15° C. or at about 5° C. The solution is adjusted to a pH of between about 5 and about 7, such as to a pH of about 5.5 to about 6.5 or to a pH of about 6.0, prior to lyophilization. Both, the process of forming the solution and the subsequent lyophilization can be carried out in darkness or in low-actinic vessels, so that the exposure of the C-21 modified epothilones to light is minimized. Exposure to light may be limited to less than 24 hours of ambient room light, or the equivalent. Preferably, the lyophilization is carried out in such a manner that the C-21 modified epothilone analogs remain exposed to an aqueous medium of pH greater than about 3.5, for less than 36 hours. This period of exposure may be limited, for example, by using appropriately-scaled equipment, or by preparing relatively small batches, and the pH may be controlled by an appropriate choice of buffer components.

The primary drying stage in the lyophilization of a solution of a C-21 modified epothilone formed as described herein may be carried out at temperatures from about −20° C. to about −10° C., such as at about −15° C., under high vacuum. The vacuum is from about 50 millitorr to 250 millitorr, for example, at about 150 millitorr, and the temperature and vacuum are maintained for an extended period, for example, from about 24 to about 72 hours, such as, for about 48 hours. Lyophilization in this temperature range has been found to produce an amorphous and rapidly soluble lyophile, which is desirable for a parenteral preparation. Those of ordinary skill in the art will appreciate that conventional procedures, such as powder X-ray diffraction, can be utilized to confirm the amorphous nature of the lyophile. If the epothilone is sufficiently soluble, a crystalline lyophile could also be used.

The residual solvents in the product may be removed by a secondary drying stage that is carried out at temperatures ranging from about −10° C. to about 30° C., for example, at about 25° C., under high vacuum. The vacuum ranges from about 50 millitorr to about 250 millitorr, for example, at about 150 millitorr, and is maintained for an extended period, for example, from about 18 to about 72 hours, such as, for about 24 hours.

Suitable diluents are well known to those of ordinary skill in the art. The present invention also provides for packaging a C-21 modified epothilone lyophile of the invention with a container containing sufficient parenteral diluent to prepare the final concentration for administration. Example of a diluent is Sterile Water For Injection. Another example of a diluent is 0.9% Sodium Chloride Injection, USP. The final solution for administration contains from about 0.01 mg/ml to about 20 mg/ml, for example, from about 0.05 mg/ml to about 10 mg/ml, such as, from about 0.05 mg/ml to about 5 mg/ml, of the C-21 modified epothilone.

A reconstituted preparation according to the present invention, e.g., a solution of the C-21 modified epothilone in Water for Injection or when further diluted with 0.9% Sodium Chloride Injection, can be stored for up to about 24 hours at room temperature and under ordinary indoor illumination. The final dilution may be administered by intravenous infusion, typically over a period of up to an hour, or by oral administration with a pharmaceutically acceptable acid neutralizing buffer.

The compositions of the invention may be provided in the form of unit doses in sealed vials, for example, glass vials or Type I glass vials closed with elastomer stoppers. The unit dose may contain a pharmaceutically effective amount of a C-21 modified epothilone derivative, together with the carboxylic acid and dextran polymer present in the lyophilized composition.

The amount of C-21 modified epothilone derivative will be dependent upon the potency of the particular C-21 modified epothilone derivative in the composition. For example, where the 21-amino epothilone derivative is [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4,17-dioxabicyclo[14.1.0]heptadecane-5,9-dione (Compound A or epothilone of formula Ic), the unit dose may contain between about 5 mg and about 20 mg of the 21-amino epothilone derivative, together with between about 10 mg and about 25 mg of citric acid and between about 50 mg and about 150 mg of dextran 40. In another embodiment, the unit dose may contain between about 9 mg and about 12 mg of the 21-amino epothilone derivative of formula Ic, together with between about 12.5 mg and about 16.7 mg of citric acid and between about 99 mg and about 132 mg of dextran 40. In yet another embodiment, the amount of the epothilone compound of formula Ic is about 11 mg, together with about 13.9 mg of citric acid and about 110 mg of dextran 40, so as to deliver about 10 mg of the 21-amino epothilone derivative of formula Ic, together with about 12.6 mg of citric acid and about 100 mg of dextran 40, after VNS losses due to reconstitution, withdrawal, and transfer of the unit dose.

Certain C-21 modified epothilones of formula I, Ia, Ib and Ic demonstrate aqueous solubility. For example, the epothilone of formula Ic is water soluble and hence can be formulated without using surfactants. The epothilones of formula Ic may be formulated without the use of surfactants to a concentration of about at least 20 mg/mL with pH adjustment. If formulations containing a surfactant are desired, the lyophilized epothilone analogs represented by formula I, Ia, Ib and Ic are reconstituted with a mixture of equal parts by volume of Dehydrated Alcohol, USP and a nonionic surfactant, preferably a polyoxyethylated castor oil surfactant (available from GAF Corporation, Mount Olive, N.J., under the trademark, Cremophor EL). Alternately, an oral suspension can be prepared by pH adjustment and the use of a stabilizer, surfactant, and/or viscosity enhancing agent, and may be administered alone or with water or with a pharmaceutically acceptable acid neutralizing buffer.

The lyophilized product and vehicle for reconstitution may be packaged separately in appropriately light-protected vials. To minimize the amount of surfactant in the reconstituted solution for parenteral administration, only a sufficient amount of the vehicle may be provided to form a solution having a concentration of about 2 mg/mL to about 4 mg/mL of the epothilone analog. Once dissolution of the drug is achieved, the resulting solution may be further diluted prior to injection with a suitable parenteral diluent. Such diluents are well known to those of ordinary skill in the art. These diluents are generally available in clinical facilities. It is, however, within the scope of the present invention to package the subject epothilone analogs with sufficient parenteral diluent to prepare the final concentration for administration, and/or with a pharmaceutically acceptable buffer for oral administration. An example of a diluent is Sterile Water for Injection. Another example of a diluent is Lactated Ringer's Injection. The final concentration for administration would contain from about 0.1 mg/mL to about 0.9 mg/mL of the epothilone analog, and less than about 20 mg/mL for oral administration.

The final dilution of the reconstituted epothilone analog in the formulation of the invention may be carried out with other preparations having similar utility, for example, 5% Dextrose Injection, Lactated Ringer's and Dextrose Injection, Sterile Water for Injection, and the like. For oral administration, the final dilution may be carried out with the same and/or with viscosity enhancing agents, polymeric stabilizers, and/or with pharmaceutically acceptable surfactants.

If the epothilone compound of the present invention is reconstituted using water, the solution can be stored for up to about 24 hours before being further diluted for administration.

The present invention is also directed to methods of treating cancer and other hyperproliferative diseases in patients comprising administering to the patient a therapeutically effective amount of one or more compounds represented by formula I, Ia, Ib and Ic. The compounds of formula I, Ia, Ib and Ic may be administered intravenously or orally. Compounds of formula I, Ia, Ib and Ic may be administered with one or more additional agents to prevent nausea, hypersensitivity, or gastric irritation, such as an anti-emetic or an $H_1$ or $H_2$ antihistamine.

The amount of a compound represented by formula I, Ia, Ib or Ic administered by each IV infusion, or orally, or both, may be determined by one of ordinary skill in the art, and includes exemplary dosage amounts for a human of from about 0.01 mg/kg/day to about 200 mg/kg/day, for example, from about 0.05 mg/kg/day to about 50 mg/kg/day, which may be administered in a single dose or in the form of individual divided doses, such as from 1 to about 4 times per day. Compounds of the present invention may be administered in a dosage of less than about 100 mg/kg/day, such as, less than about 50 mg/kg/day in a single dose or in 1 to about 4 divided doses. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Subjects for treatment include animals, for example, mammalian species such as humans, and domestic animals such as dogs, cats and the like, subject to the aforementioned disorders.

Typically the compounds of formula I, Ia, Ib and Ic are administered until the patient shows a response, for example, a reduction in tumor size, or until dose-limiting toxicity is reached. One or ordinary skill in the art will readily know when a patient shows a response or when dose limiting toxicity is reached. The common dose-limiting toxicities associated with compounds of formula I, Ia, Ib and Ic include, but are not limited to, fatigue, arthralgia/myalgia, anorexia, hypersensitivity, neutropenia, thrombocytopenia, and neurotoxicity.

When administered intravenously, the compounds of formula I, Ia, Ib or Ic may be administered using the formulations of the invention. Generally, the compounds of formula I, Ia, Ib and Ic may be administered by IV infusion over a period of from about 10 minutes to about 3 hours, for example, about 45 minutes to about 2 hours. As further examples, the compounds of formula I, Ia, Ib and Ic may be administered by IV infusion over a period of from about 30 minutes to about 90 minutes, or from about 15 minutes to about 45 minutes. Typically, the compounds are administered intravenously in a dose of from about 0.5 mg/m$^2$ to about 100 mg/m 2, for example, about 1 mg/m$^2$ to about 70 mg/m$^2$, or about 10 mg/m$^2$ to about 70 mg/m$^2$. In one embodiment, the compounds of formula I, Ia, Ib or Ic are administered intravenously in a dose of about 10 mg/m$^2$ to about 65 mg/m$^2$, such as, for example, about 50 mg/m$^2$.

One of ordinary skill in the art would readily know how to convert doses from mg/kg to mg/m2 given either or both the height and or weight of the patient. (See, e.g., http://www.fda.gov/cder/cancer/animalframe.htm.)

As discussed above, a compound of formula I, Ia, Ib or Ic can be administered orally, intravenously, or both. In particular, the methods of the invention encompass dosing protocols such as once a day for 2 to 10 days, for example, every 3 to 9 days, every 4 to 8 days, or every 5 days. In one embodiment there is a period of 3 days to 5 weeks, for example, 4 days to 4 weeks, 5 days to 3 weeks, or 1 week to 2 weeks, in between cycles where there is no treatment. In another embodiment a compound of formula I, Ia, Ib or Ic can be administered orally, intravenously, or both, once a day for 3 days, with a period of, for example, 1 week to 3 weeks in between cycles where there is no treatment. In yet another embodiment a compound of formula I, Ia, Ib or Ic can be administered orally, intravenously, or both, once a day for 5 days, with a period of, for example, 1 week to 3 weeks in between cycles where there is no treatment.

In one embodiment, the treatment cycle for administration of a compound of formula I, Ia, Ib or Ic is once daily for 3 consecutive days and the period between treatment cycles is from about 2 to about 10 days, such as, for example, one week. In another embodiment, the treatment cycle for administration of a compound of formula I, Ia, Ib or Ic is once daily for 5 consecutive days and the period between treatment cycles is from about 2 to about 10 days, such as, for example, one week.

A compound of formula I, Ia, Ib or Ic can also be administered orally, intravenously, or both once every 1 to 10 weeks, such as, every 2 to 8 weeks. For example, a compound of formula I, Ia, Ib or Ic can also be administered orally, intravenously, or both, once every 3 to 6 weeks, such as once every 3 weeks.

In another method of the invention, a compound of formula I, Ia, Ib or Ic is administered in a 28 day cycle wherein the compound of formula I, Ia, Ib or Ic is intravenously administered on days 1, 7, and 14 and orally administered on day 21. Alternatively, a compound of formula I, Ia, Ib or Ic is administered in a 28 day cycle wherein the compound of formula I, Ia, Ib or Ic is orally administered on day 1 and intravenously administered on days 7, 14, and 28.

According to the methods of the invention, a compound of formula I, Ia, Ib or Ic is administered until the patient shows a response, for example, a reduction in tumor size, or until dose limiting toxicity is reached.

Many anti-cancer agents are neurotoxic, e.g., they are known to cause side effects of the central and peripheral nervous system. This invention further encompasses the use of compounds of formula I, Ia, Ib and Ic in patients previously experiencing neurotoxicity with other anti-cancer agents. Although, the compounds of the invention may also cause neurotoxicity at certain doses, the methods herein can be used to reduce or avoid such toxicity.

By way of illustration, and without serving as limitations in any way, the following examples serve to illustrate the practice of the invention.

EXAMPLES

Example 1

Formulation Containing a C-21 Modified Epothilone

Using the methods described herein, a number of formulations were prepared and examined for the stability of the 21-aminoepothilone derivative, to determine the effect of various buffers and bulking agents on solution and lyophile stability. For the lyophilized product, attention was focused on excipients that would facilitate the diffusive loss of water by rendering the cake porous and/or would be sufficiently hygroscopic to absorb residual moisture away from the active compound. The buffer was used to maintain a pH of about 5–6. The buffers evaluated included bicarbonate, citrate and succinate, and the bulking agents evaluated included mannitol, dextran 40, histidine, lysine and sodium chloride. Based on the results of stability studies, a citrate-buffered formulation containing dextran 40 was selected for further studies.

Example 2

Stability of Epothilone Formulation

A citrate-buffered formulation containing dextran 40 was manufactured as in Example 1 above. Samples in 15-mL Type I glass vials (11 mg epothilone derivative per vial), with 20-mm bromobutyl Omniflex® coated stoppers, were placed on stability at 5° C., 25° C. and 40° C. for six months. During the six months of storage, there were no changes in lyophile appearance for any of the samples and there were no changes in the measured pH of reconstituted lyophile samples. There were no changes in potency or total impurities for samples stored at 5° C. After six months at 25° C. and 40° C., potency decreased by 3% and 10% respectively, accompanied by increases in total impurities. Other experiments showed that the drug product was sensitive to exposure to light. Based on the results of stability studies, it is preferred that the lyophile be stored at 2° C. to 8° C., protected from light.

Example 3

Formulation Containing an Epothilone of Formula Ic

[1S-[1R*,3R*(E),7R*,10S*,11R*,12R*,16S*]]-3-[2-[2-(Aminomethyl)-4-thiazolyl]-1-methylethenyl]-7,11-dihydroxy-8,8,10,12,16-pentamethyl-4,17-dioxabicyclo[14.1.0]heptadecane-5,9-dione (compound of formula Ic) (8.7 g) was dissolved in 1280 mL of an aqueous solution of citric acid (10.1 grams) and dextran 40 (80 grams) which had been pre-cooled to about 5° C. Once the drug powder had become completely dissolved, the solution pH was adjusted to 6.0 and Water for Injection (178 mL) was added.

The solution formed above was promptly lyophilized in a Virtis Genesis(TM) lyophilizer at −15° C. with exclusion of light over a period of 34 hours. The resultant lyophile was then further dried at 25° C. under high vacuum for 24 hours. No detectable degradation of the drug was observed during these procedures. The lyophile was packaged under clean conditions into 15 mL vials, each containing 10 mg of drug plus a 10% excess to allow for transfer and dispensing (vial/needle/syringe, VNS) losses.

The lyophile in a single vial is reconstituted with 5.4 mL of Sterile Water for Injection, USP, to achieve a final drug concentration of 2 mg/mL. Once dissolution is effected by gently swirling the vial, the resultant solution is diluted to achieve a concentration of 0.1 mg/mL by the addition of 20 mL of 0.9% Sodium Chloride Injection per mL of constituted drug product.

Example 4

Formulation Without Citric Acid or Without a Dextran Polymer

The above procedure was followed, but omitting the citric acid.

The above procedure was also followed, but omitting the dextran polymer.

Example 5

Formulation Without Citric Acid and Dextran 40

The procedure of Example 1 was followed, but omitting both the citric acid and the dextran 40. This was the control sample, containing drug alone.

Example 6

Formulation Using Mannitol

The procedure of Example 1 was followed, but omitting the citric acid, and using mannitol in place of the dextran 40.

Example 7

Formulation Using L-lysine

The procedure of Example 1 was followed, but omitting the citric acid, and using L-lysine in place of the dextran 40.

Example 8

Formulation Using Sodium Succinate

The procedure of Example 1 was followed, but omitting the dextran 40, and using sodium succinate in place of the citric acid.

The lyophilized powders of examples 3–8 were stored and examined for stability.

Example 9

Synthesis of Epothilone of Formula Ic

Method for the synthesis of the epothilone of formula Ic is described in U.S. Pat. No. 6,262,094, issued Jul. 17, 2001, the entire contents of which are herein incorporated by reference.

Conversion of Epothilone B to Epothilone F

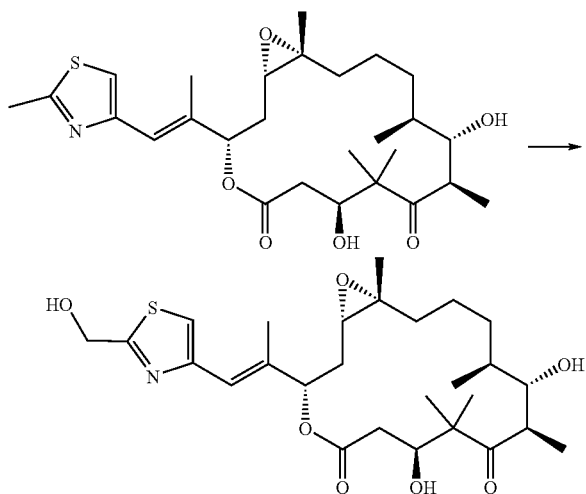

(i) 1.98 g (3.90 mmol) of Epothilone B was placed under Argon and dissolved in 60 mL dry $CH_2Cl_2$. To this solution was added 0.720 g mCPBA (4.17 mmol, 1.07 equivalents). The mixture was allowed to stir at 25° C. for 5.5 hours. The reaction mixture was quenched with 60 mL $NaHCO_3$, and extracted with 3×75 mL of $CHCl_3$. The organic phase was washed with 100 mL water followed by 70 mL of 5% $Na_2SO_{3(aq)}$ and then 70 mL brine. The organic phase was then dried over $Na_2SO_4$. The crude reaction product was chromatographed using silica gel eluting with 2% MeOH in $CHCl_3$ to yield 0.976 g of the N-oxide (48%) as a white fluffy solid.

(ii) To a resealable tube under Argon was added 0.976 g of the N-oxide (1.86 mmol) dissolved in 35 mL dry $CH_2Cl_2$, 2,6-lutidine (1.73 mL, 14.88 mmol, 8 equivalents) and $(CF_3CO)_2O$ (1.84 mL, 13.02 mmol, 7 equivalents). The tube was sealed and heated at 70° C. for 25 min. The mixture was allowed to cool and the solvent was removed under a stream of argon, followed by concentration to a few mL of dark yellow solution under vacuum. The reaction was diluted with 25 mL MeOH and 2.9 mL of 28% $NH_4OH_{(aq)}$ was added. The mixture was heated to 45° C. for 20 min, then cooled to room temperature. The crude product was concentrated on the rotary evaporator and chromatographed using silica gel eluting with 4% MeOH in $CHCl_3$ to yield 0.815 g of Epothilone F (84%).

Synthesis of 21-azido-epothilones

Example: [1S-[1R*,3R*(E),7R*,10S*,11R*,12R*,16S*]]-3-[2-[2-(Azidomethyl)-4-thiazolyl]-1-methylethenyl]-7,11-dihydroxy-8,8,10,12,16-pentamethyl-4,17-dioxabicyclo[14.1.0]heptadecane-5,9-dione.

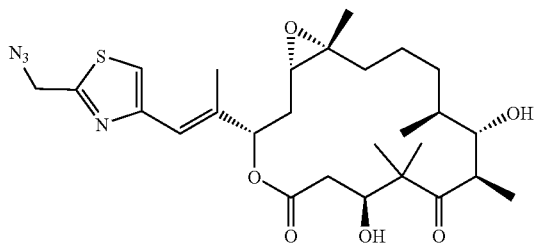

To a stirred solution of epothilone F from above (957 mg, 1.83 mmol) in 20.0 mL tetrahydrofuran at 0° C. under Argon was added 0.47 mL diphenylphosphoryl azide (604 mg, 2.19 mmol, 1.2 equivalents). The mixture was stirred for approximately 3 min. 1,8-diazabicyclo[5.4.0]undec-7-ene (0.27 mL, 278 mg, 1.83 mmol, 1 equivalents) was then added and the mixture was stirred at 0° C. After 2 hours, the mixture was warmed to 25° C. and stirred for 20 hours. The reaction mixture was diluted with 150 mL ethyl acetate and washed with 50 mL $H_2O$. The aqueous layer was extracted with 35 mL ethyl acetate. The combined organic layers were dried over $Na_2SO_4$ and concentrated under vacuum. The crude material was chromatographed using silica gel eluted with 50% ethyl acetate in hexanes to afford 913 mg (91%) of 21-azido-epothilone B, as a clear, colorless oil. MS (ESI+): 549.3 (M+H)+; $^1$H-NMR (300 MHz, $CDCl_3$); δ=6.59 (bs, 17-H), 7.04 (s, 19-H), 4.63 (s,21-$H_2$); HRMS (DCI); $C_{27}H_{40}N_4O_6S$: [M+] calculated 549.2747, found 549.2768.

Synthesis of 21-amino-epothilones

Example: [1S-[1R*,3R*(E),7R*,10S*,11R*,12R*,16S*]]-3-[2-[2-(Aminomethyl)-4-thiazolyl]-1-methylethenyl]-7,11-dihydroxy-8,8,10,12,16-pentamethyl-4,17-dioxabicyclo[14.1.0]heptadecane-5,9-dione (Compound of formula Ic or Compound A).

Lindlar catalyst, 18.0 mg, was suspended in 500 μL of ethanol in an $H_2$ atmosphere and was saturated. Then, 15.9 mg (29.0 μmol) of 21-azido-epothilone B from above, dissolved in an ethanol-methanol mixture, was added. After stirring for 30 minutes at room temperature, the suspension is filtered through Celite, and washed with ethyl acetate. The solvent was removed from the organic phase and dried in high vacuum. The purification of the crude product was done through PSC (solvent:$CH_2Cl_2$/methanol 90:10), whereupon 12.3 mg (81%) of 21-amino-epothilone B and 1 mg (6%) of educt is obtained.

$^1$H-NMR (300 MHz, $CDCl_3$); δ=6.58 (bs, 17-H), 7.05 (s, 19-H), 4.15 (s, 21-$H_2$); HRMS (DCI); $C_{27}H_{42}N_2O_6S$: [M+H+] calculated 522.2764, found 522.2772.

Synthesis of 21-amino-epothilones (Alternative)

[1S-[1R*,3R*(E),7R*,10S*,11R*,12R*,16S*]]-3-[2-[2-(Aminomethyl)-4-thiazolyl]-1-methylethenyl]-7,11-dihydroxy-8,8,10,12,16-pentamethyl-4,17-dioxabicyclo[14.1.0]heptadecane-5,9-dione

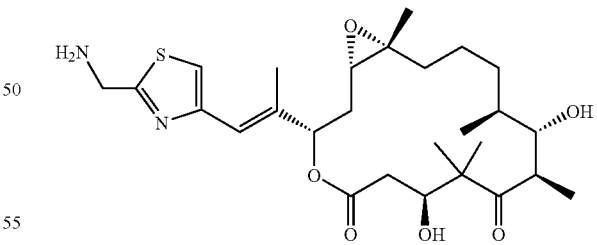

To a stirred solution of 21-azido-epothilone B from above (1.070 g, 1.950 mmol) in 30.0 mL tetrahydrofuran under Argon was added 0.22 mL of trimethylphosphine (0.163 g, 2.145 mmol, 1.1 equivalents). $H_2O$ (5.5 mL) was then added, and the mixture was allowed to stir at 25° C. After 3 hours, the azide was completely consumed and 3 mL of 28% aqueous $NH_4OH_{(aq)}$ was added to complete the conversion of phosphoryl imine to amine. After stirring at 25° C. for 1 hour the solvents were removed under vacuum. The crude material was chromatographed using silica gel eluted with 1% Et$_3$N, 2.5% MeOH in CHCl$_3$ to yield 924 mg (91%) of 21-amino-epothilone B, as a white solid. MS (ESI$^+$): 523.3 (M+H)$^+$ Example 10

Lyophilized Formulation of Epothilone of Formula Ic

1. Stability

Initially, determination of the effect of various buffers and bulking agents on solution and lyophile stability of the formulation of compound of formula Ic (Compound A) was performed. For the lyophilized product, the goal was to minimize free water available to Compound A by selecting excipients that would facilitate the diffusive loss of water from the lyophile by rendering the cake porous or by using excipients that would be sufficiently hygroscopic to absorb the residual moisture away from the active compound. The buffer was used to maintain a pH of about 6, but could include pH greater than about 4. The buffers evaluated include bicarbonate, citrate and succinate and the bulking agents evaluated include mannitol, dextran 40, histidine, lysine and sodium chloride. Based on stability data, a citrate buffered formulation containing dextran 40 was found to be preferable.

2. Composition of Formulation

Compound A formulation, 10 mg/vial, is a sterile, non-pyrogenic lyophilized product which appears as a white to off-white, whole or fragmented cake. In addition to the active ingredient, the lyophilized drug product contains 13.9 mg of citric acid and 10 mg of dextran 40 per vial. The pH of the bulk solution was adjusted with sodium hydroxide and/or hydrochloric acid to pH 6.0, prior to lyophilization. The quantitative composition for the formulation is presented in Table 1. A sufficient excess of drug was provided in each vial to allow for withdrawal losses. The drug product was packaged in Type I glass vials, stoppered with 20 mm closures and sealed with aluminum seals.

TABLE 1

Quantitative Composition of Compound A Formulation

| Ingredient | Ingredient Code | Amount per mL | Amount per Vial |
| --- | --- | --- | --- |
| BMS-310705-01 | N/A | 5.0 mg | 11.0 mg (1) |
| Dextran 40 USP | RM2002 | 50.0 mg | 110 mg |
| Citric Acid USP | 30061 | 6.3 mg | 13.9 mg |
| Sodium Hydroxide NF/ | 40230/ | qs ad pH 6.0 | qs ad pH 6.0 |
| Hydrochloric Acid NF | 10704 | | |
| Water for Injection USP | 20445 | qs ad 1.0 mL | qs ad 2.20 mL (2) |

(1) At 100% purity and includes a 10% overfill for VNS losses.
(2) Removed during lyophilization.

3. Longer Term Stability of Compound A Formulation

Compound A formulation, 10 mg/vial was manufactured and placed on stability at 5° C., 25° C. and 40° C. The package components used for this batch, 15-mL Type I glass vials and 20-mm bromobutyl Omniflex® coated stoppers, were also used to package the clinical material. Stability of samples of drug product stored at various temperature conditions for six months was evalauted. During the six months of storage, there were no changes in lyophile appearance for any of the samples and there were no changes in the appearance or pH of solution from constituted lyophile samples. Stability data demonstrated that there were no changes in Compound A potency or total impurities for samples stored at 5° C. At 25° C. and 40° C., however, there were potency losses of 3% and 10%, respectively, and these losses in potency were accompanied by increases in total impurities. Stability data also showed that the drug product was sensitive to light exposure. Based on these stability results, it is preferred that a Compound A formulation be stored at 2° C. to 8° C., protected from light.

4. Reconstitution

Compound A formulation, 10 mg/vial, is constituted with Sterile Water for Injection, USP (SWFI), prior to use. The drug product was constituted by slowly injecting 5.4 mL of SWFI into the vial of BMS-310705-01 for Injection, 10 mg/vial. The vial was gently swirled until the lyophile was completely dissolved. When the lyophile was completely dissolved, the vial contained 5.5 mL of solution with a Compound A concentration of 2 mg/mL. This solution, resulting from constitution of the lyophile, must be further diluted with 0.9% Sodium Chloride Injection, USP to a final Compound A concentration ranging from 0.05 mg/mL to 2 mg/mL prior to administration to the patient. The infusion is to be administered through a 5 micron in-line filter extension set (B. Braun Medical Inc., Product Code FE-5010Y) and must be completed within 24 hours of lyophile constitution.

5. Storage of Compound A Formulation

Compound A formulation should be stored refrigerated (2° to 8° C.) and protected from light prior to use. After initial constitution with Sterile Water for Injection, USP, the constituted product may be stored in the vial at 5° C. or at room temperature and room light for a maximum of 24 hours. In addition, after final dilution with 0.9% Sodium Chloride Injection, USP, solutions of Compound A are stable when stored at 5° C. or at room temperature and room light for a maximum of 24 hours. Following constitution of the lyophilized drug product, all constituted and/or diluted solutions must be used within 24 hours.

Example 11

Use of Compound A (Epothilone of Formula Ic)

Compound A demonstrated anticancer activity in taxane-sensitive and taxane-resistant tumor models. Furthermore, Compound A is water soluble and hence it was not necessary to formulate it using a nonionic surfactant such as Cremophor EL.

Compound A was administered to human patients once every three (3) weeks as a 15-minute infusion, using an accelerated followed by modified Fibonacci dose escalation design. Twenty-two (22) patients were treated at does levels of 0.6, 1.2, 2.5, 5, 10, 20, 30 and 40 mg/m$^2$. Preliminary pharmacokinetics showed increases in AUC and CMAX, both of which are dose-related, and were similar between cycle 1 and cycle 2.

For the 30 mg/m$^2$ dose level in cycle 1, the mean pharmacokinetic parameter values (n=7) were CMAX 3433 ng/mL; AUC 2105 ng.h/mL; $t_{1/2}$ 33 hours; $Cl_t$ 282 mL/min/m$^2$; and $V_{ss}$ 494 L/m$^2$.

In four of the seven patients in the 30 mg/m2 cohort, the plasma concentrations achieved were near or above the preclinically determined effective concentration (MEC) for about 8 hours, suggesting that the drug exposure approached the efficacious range. Related toxicities include diarrhea, nausea, vomitting, anorexia, fatigue, anemia, alopecia, neuropathy, myalgia and neutropenia. No dose-limiting toxicity (DLT) was observed.

The embodiments of the invention described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A pharmaceutical composition comprising:
a) a C-21 modified epothilone compound of formula I:

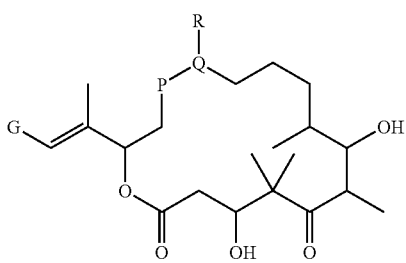

wherein:
P-Q is a C,C double bond or an epoxide;
G is

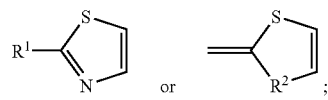

R is selected from the group consisting of H, alkyl, and substituted alkyl;
$R^1$ is selected from the group consisting of

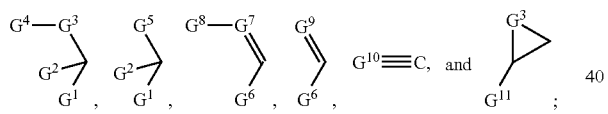

$R^2$ is

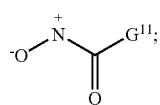

$G^1$ is selected from the group consisting of H, halogen, CN, alkyl and substituted alkyl;
$G^2$ is selected from the group consisting of H, alkyl, and substituted alkyl;
$G^3$ is selected from the group consisting of O, S, and $NZ^1$;
$G^4$ selected from the group consisting of H, alkyl, substituted alkyl, $OZ^2$, $NZ^2Z^3$, $Z^2C=O$, $Z^4SO_2$, and optionally substituted glycosyl;
$G^5$ is selected from the group consisting of halogen, $N_3$, NCS, SH, CN, NC, $N(Z^1)_3^+$ and heteroaryl;
$G^6$ is selected from the group consisting of H, alkyl, substituted alkyl, $CF_3$, $OZ^5$, $SZ^5$, and $NZ^5Z^6$;
$G^7$ is $CZ^7$ or N;
$G^8$ is selected from the group consisting of H, halogen, alkyl, substituted alkyl, $OZ^{10}$, $SZ^{10}$, and $NZ^{10}Z^{11}$;
$G^9$ selected from the group consisting of O, S, —NH— NH— and —N=N—;
$G^{10}$ is N or $CZ^{12}$;
$G^{11}$ is selected from the group consisting of $H_2N$, substituted $H_2N$, alkyl, substituted alkyl, aryl, and substituted aryl;
$Z^1$, $Z^6$, $Z^9$, and $Z^{11}$ are independently selected from the group consisting of H, alkyl, substituted alkyl, acyl, and substituted acyl;
$Z^2$ is selected from the group consisting of H, alkyl, substituted alkyl, aryl, substituted aryl, and heterocyclic;
$Z^3$, $Z^5$, $Z^8$, and $Z^{10}$ are independently selected from the group consisting of H, alkyl, substituted alkyl, acyl, substituted acyl, aryl, and substituted aryl;
$Z^4$ is selected from the group consisting of alkyl, substituted alkyl, aryl, substituted aryl, and heterocyclic;
$Z^7$ is selected from the group consisting of H, halogen, alkyl, substituted alkyl, aryl, substituted aryl, $OZ^8$, $SZ^8$, and $NZ^8Z^9$; and
$Z^{12}$ is selected from the group consisting of H, halogen, alkyl, substituted alkyl, aryl, and substituted aryl;
with the proviso that when $R^1$ is

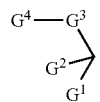

$G^1$, $G^2$, $G^3$ and $G^4$ cannot simultaneously have the following meanings:
$G^1$ and $G^2$=H, $G^3$=O and $G^4$=H or $Z^2C=O$ where $Z^2$=alkyl, and with the proviso that when $R^2$ is

$G^1$, $G^2$ or $G^5$ cannot simultaneously have the following meanings: $G^1$ and $G^2$=H, and $G^5$=F;
or a pharmaceutically acceptable salt, solvate, clathrate, hydrate or prodrug thereof;
b) a dibasic carboxylic acid; and
c) a dextran polymer.

2. The composition of claim 1 wherein said C-21 modified epothilone compound is of formula Ia:

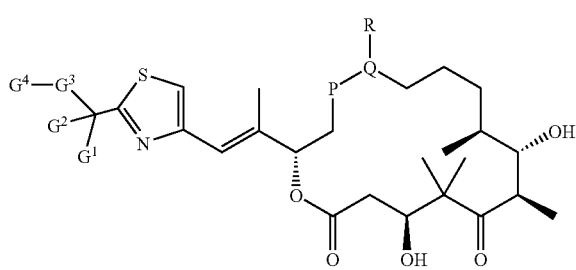

wherein:
P-Q is a C,C double bond or an epoxide,
R is H or methyl,
$G^1$ is H, alkyl, substituted alkyl, or halogen,
$G^2$ is H, alkyl, or substituted alkyl, $G^3$ is O, S, or $NZ^1$, $Z^1$ is H, alkyl, substituted alkyl, acyl, or substituted acyl, $G^4$ is H, alkyl, substituted alkyl, $OZ^2$, $NZ^2Z^3$, $Z^2C=O$, $Z^4SO_2$, or optionally substituted glycosyl, $Z^2$ is H, alkyl, substituted alkyl, aryl, substituted aryl, or heterocyclic, $Z^3$ is H, alkyl, substituted alkyl, acyl, or substituted acyl, and $Z^4$ is alkyl, substituted alkyl, aryl, substituted aryl, or heterocyclic, with the proviso that $G^1$, $G^2$, $G^3$ and $G^4$ cannot have simultaneously the following meanings: $G^1$ and $G^2$=H, $G^3$=O and $G^4$=H or $Z^2C=O$ with $Z^2$=alkyl;

or a pharmaceutically acceptable salt, solvate, clathrate, hydrate or prodrug thereof.

3. The composition of claim 2 wherein said C-21 modified epothilone compound is of formula Ib:

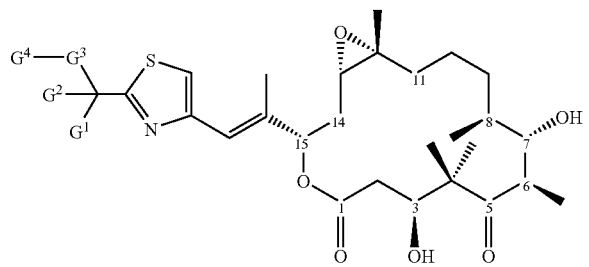

Ib wherein:

$G^1$ is H, alkyl, substituted alkyl, or a halogen, $G^2$ is H, alkyl, or substituted alkyl, $G^3$ is O, S, or $NZ^1$, $Z^1$ is H, alkyl, substituted alkyl, acyl, or substituted acyl, $G^4$ is H, alkyl, substituted alkyl, $OZ^2$, $NZ^2Z^3$, $Z^2C=O$, $Z^4SO_2$, or optionally substituted glycosyl, $Z^2$ is H, alkyl, substituted alkyl, aryl, substituted aryl, or heterocyclic, $Z^3$ is H, alkyl, substituted alkyl, acyl, or substituted acyl, and $Z^4$ is alkyl, substituted alkyl, aryl, substituted aryl, or heterocyclic;

or a pharmaceutically acceptable salt, solvate, clathrate, hydrate or prodrug thereof.

4. The composition of claim 3 wherein said C-21 modified epothilone compound is of formula Ic:

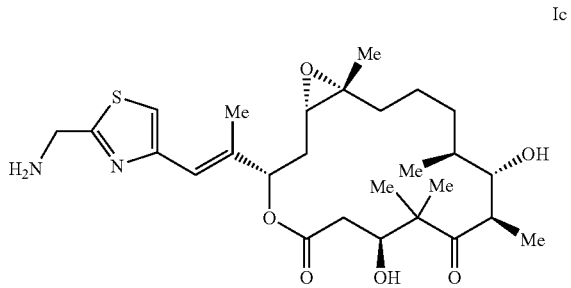

Ic or a pharmaceutically acceptable salt, solvate, clathrate, hydrate or prodrug thereof.

5. The composition of claim 1 prepared by a method comprising lyophilizing an aqueous solution comprising said C-21 modified epothilone compound, said dibasic carboxylic acid, and said dextran polymer.

6. The composition of claim 5 wherein said aqueous solution is adjusted to a pH of between about 5 and about 7.

7. The composition of claim 1 wherein said dextran polymer is dextran 40.

8. The composition of claim 1 wherein said dibasic carboxylic acid is succinic acid.

9. The composition of claim 1 wherein said dibasic carboxylic acid is citric acid.

10. The composition of claim 1 wherein said dextran polymer is dextran 40 and said dibasic carboxylic acid is succinic acid.

11. The composition of claim 1 wherein said dextran polymer is dextran 40 and said dibasic carboxylic acid is citric acid.

12. The composition of claim 4 prepared by a method comprising lyophilizing an aqueous solution comprising said C-21 modified epothilone compound, said dibasic carboxylic acid, and said dextran polymer.

13. The composition of claim 12 wherein said aqueous solution is adjusted to a pH of between about 5 and about 7.

14. The composition of claim 4 wherein said dextran polymer is dextran 40.

15. The composition of claim 4 wherein said dibasic carboxylic acid is succinic acid.

16. The composition of claim 4 wherein said dibasic carboxylic acid is citric acid.

17. The composition of claim 4 wherein said dextran polymer is dextran 40 and said dibasic carboxylic acid is succinic acid.

18. The composition of claim 4 wherein said dextran polymer is dextran 40 and said dibasic carboxylic acid is citric acid.

19. A method of preparing a pharmaceutical composition comprising the steps of:

(a) preparing an aqueous solution containing a C-21 modified epothilone compound of formula I, a dibasic carboxylic acid, and a dextran polymer;

(b) adjusting the pH of said solution to between about 5 and about 7;

(c) lyophilizing said solution of step (b) to form a lyophile; and (d) drying said lyophile of step (c)

wherein said C-21 modified epothilone compound of formula I is:

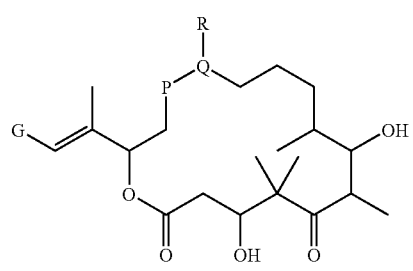

I wherein:

P-Q is a C,C double bond or an epoxide;

G is

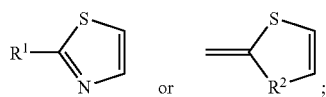

R is selected from the group consisting of H, alkyl, and substituted alkyl;
$R^1$ is selected from the group consisting of

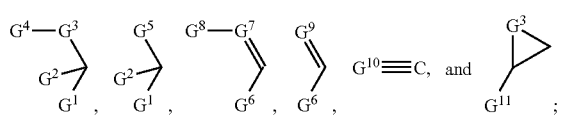

$R^2$ is

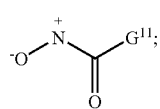

$G^1$ is selected from the group consisting of H, halogen, CN, alkyl and substituted alkyl;
$G^2$ is selected from the group consisting of H, alkyl, and substituted alkyl;
$G^3$ is selected from the group consisting of O, S, and $NZ^1$;
$G^4$ is selected from the group consisting of H, alkyl, substituted alkyl, $OZ^2$, $NZ^2Z^3$, $Z^2C$=O, $Z^4S_2$, and optionally substituted glycosyl;
$G^5$ is selected from the group consisting of halogen, $N_3$, NCS, SH, CN, NC, $N(Z^1)_3^+$ and heteroaryl;
$G^6$ is selected from the group consisting of H, alkyl, substituted alkyl, $CF_3$, $OZ^5$, $SZ^5$, and $NZ^5Z^6$;
$G^7$ $CZ^7$ or N;
$G^8$ is selected from the group consisting of H, halogen, alkyl, substituted alkyl, $OZ^{10}$, $SZ^{10}$, and $NZ^{10}Z^{11}$;
$G^9$ is selected from the group consisting of O, S, —NH—NH— and —N=N—;
$G^{10}$ is N or $CZ^{12}$;
$G^{11}$ is selected from the group consisting of $H_2N$, substituted $H_2N$, alkyl, substituted alkyl, aryl, and substituted aryl; $Z^1$, $Z^6$, $Z^9$, and $Z^{11}$ are independently selected from the group consisting of H, alkyl, substituted alkyl, acyl, and substituted acyl;
$Z^2$ is selected from the group consisting of H, alkyl, substituted alkyl, aryl, substituted aryl, and heterocyclic;
$Z^3$, $Z^5$, $Z^8$, and $Z^{10}$ are independently selected from the group consisting of H, alkyl, substituted alkyl, acyl, substituted acyl, aryl, and substituted aryl;
$z^4$ is selected from the group consisting of alkyl, substituted alkyl, aryl, substituted aryl, and heterocyclic;
$Z^7$ is selected from the group consisting of H, halogen, alkyl, substituted alkyl, aryl, substituted aryl, $OZ^8$, $SZ^8$, and $NZ^8Z^9$; and
$Z^{12}$ is selected from the group consisting of H, halogen, alkyl, substituted alkyl, aryl, and substituted aryl;

with the proviso that when $R^1$ is

$G^1$, $G^2$, $G^3$ and $G^4$ cannot simultaneously have the following meanings:
Gand $G^2$=H, $G^3$=O and $G^4$=H or $Z^2C$=O where $Z^2$=alkyl,
and with the proviso that when $R^1$ is

$G^1$, $G^2$ or $G^5$ cannot simultaneously have the following meanings: Gand $G^2$=H, and $G^5$=F;
or a pharmaceutically acceptable salt, solvate, clathrate, hydrate or prodrug thereof.

20. The method of claim 19 wherein said C-21 modified epothilone compound is of formula Ia:

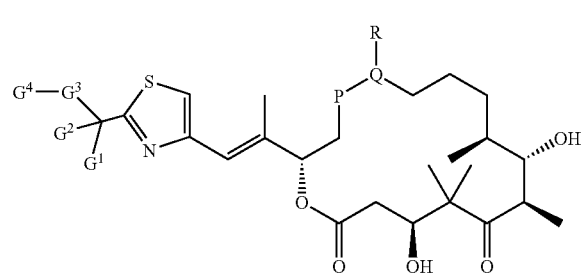

wherein:
P-Q is a C,C double bond or an epoxide,
R is a H or methyl,
$G^1$ is H, alkyl, substituted alkyl, or halogen,
$G^2$ is H, alkyl, or substituted alkyl,
$G^3$ is O, S, or $NZ^1$,
$G^4$ is H, alkyl, substituted alkyl, $OZ^2$, $NZ^2Z^3$, $Z^2C$=O, $Z^4SO_2$, or an optionally substituted glycosyl,
$Z^1$ is H, alkyl, substituted alkyl, acyl, or substituted acyl,
$Z^2$ is H, alkyl, substituted alkyl, aryl, substituted aryl, or heterocyclic,
$Z^3$ is H, alkyl, substituted alkyl, acyl, or substituted acyl, and
$Z^4$ is alkyl, substituted alkyl, aryl, substituted aryl, or heterocyclic,
with the proviso that $G^1$, $G^2$, $G^3$, and $G^4$ cannot have simultaneously the following meanings: $G^1$ and $G^2$=H, $G^3$=O, and $G^4$=H or $Z^2C$=O with $Z^2$=alkyl;
or a pharmaceutically acceptable salt, solvate, clathrate, hydrate or prodrug thereof.

21. The method of claim 20 wherein said C-21 modified epothilone compound is of formula Ib:

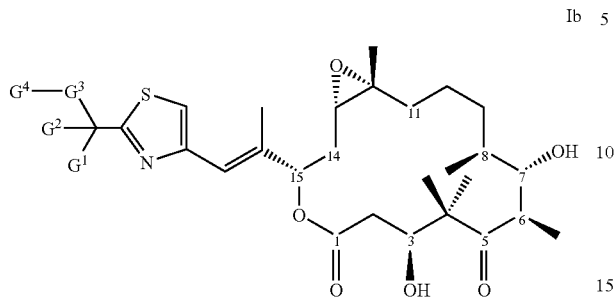

wherein:
G$^1$ is H, alkyl, substituted alkyl, or halogen,
G$^2$ is H, alkyl, or substituted alkyl,
G$^3$ is O, S, or NZ$^1$,
G4 is H, alkyl, substituted alkyl, OZ$^2$, NZ$^2$Z$^3$, Z$^2$C=O, Z$^4$SO$_2$, or an optionally substituted glycosyl,
Z$^1$ is H, alkyl, substituted alkyl, acyl, or substituted acyl,
Z$^2$ is H, alkyl, substituted alkyl, aryl, substituted aryl, or heterocyclic,
Z$^3$ is H, alkyl, substituted alkyl, acyl, or substituted acyl, and
Z$^4$ is alkyl, substituted alkyl, aryl, substituted aryl, or heterocyclic;
or a pharmaceutically acceptable salt, solvate, clathrate, hydrate, or prodrug thereof.

22. The method of claim 21 wherein said C-21 modified epothilone compound is of formula Ic:

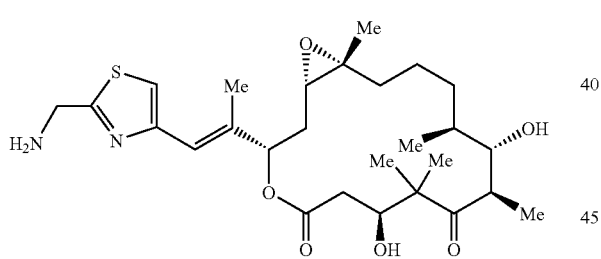

or a pharmaceutically acceptable salt, solvate, clathrate, hydrate or prodrug thereof.

23. The method of claim 19 wherein said aqueous solution is adjusted to a pH of between about 5.5 and about 6.5.

24. The method of claim 19 wherein said dextran polymer is dextran 40.

25. The method of claim 19 wherein said dibasic carboxylic acid is succinic acid.

26. The method of claim 19 wherein said dibasic carboxylic acid is citric acid.

27. The method of claim 19 wherein said dextran polymer is dextran 40 and said dibasic carboxylic acid is succinic acid.

28. The method of claim 19 wherein said dextran polymer is dextran 40 and said dibasic carboxylic acid is citric acid.

29. The method of claim 22 wherein said aqueous solution is adjusted to a pH of between about 5.5 and about 6.5.

30. The method of claim 22 wherein said dextran polymer is dextran 40.

31. The method of claim 22 wherein said dibasic carboxylic acid is succinic acid.

32. The method of claim 22 wherein said dibasic carboxylic acid is citric acid.

33. The method of claim 22 wherein said dextran polymer is dextran 40 and said dibasic carboxylic acid is succinic acid.

34. The method of claim 22 wherein said dextran polymer is dextran 40 and said dibasic carboxylic acid is citric acid.

35. A unit dose of a pharmaceutical composition comprising a sealed vial containing between about 10 mg and about 25 mg of citric acid, between about 50 mg and about 150 mg of dextran 40, and between about 5 mg and about 20 mg of [1S-[1R*,3R*(E),7R*,10S*, 11R*,12R*, 16S*]]-3-[2-[2-(aminomethyl)-4-thiazolyl]-1-methylethenyl]-7,11-dihydroxy-8,8,10,12,16-pentamethyl-4,17-dioxabicyclo[14.1.0]heptadecane-5,9-dione.

36. The unit dose according to claim 35 comprising a sealed vial containing between about 12.5 mg and about 16.7 mg of said citric acid, between about 99 mg and about 132 mg of said dextran 40, and between about 9 mg and about 12 mg of said [1S-[1R*,3R*(E),7R*,10S*,11R*, 12R*,16S*]]3-2-[2[2-(aminomethyl)-4-thiazolyl]1-methylethenyl]-7,11-dihydroxy-8,8,10,12,16-pentamethyl-4,17-dioxabicyclo[14.1.0]heptadecane-5,9-dione.

37. The unit dose according to claim 36 containing about 13.9 mg of said citric acid, about 110 mg of said dextran 40, and about 11 mg of said [1S-[1R*,3R*(E),7R*,10S*,11R*, 12R*,16S*]-3-[2-[2-(aminomethyl)-4-thiazolyl]-1-methylethenyl]-7,11-dihydroxy-8,8,10,12,16-pentamethyl-4,17-dioxabicyclo[14.1.0]heptadecane-5,9-dione.

38. A method for treating cancer in a patient, wherein said cancer is selected from the group consisting of breast, head neck, sarcoma, colorectal, UPT, melanoma, esophagus, renal, cervix, thyroid, anal, ovarian, and colon cancer, comprising administering to said patient, by intravenous or oral administration, an effective amount of a pharmaceutical composition comprising:

a) a C-21 modified epothilone compound of formula I:

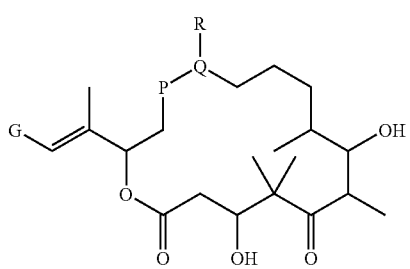

wherein:
P-Q is a C,C double bond or an epoxide;
G is

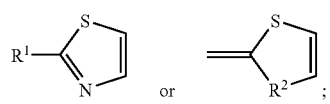

R is selected from the group of H, alkyl, and substituted alkyl;

R[1] is selected from the group consisting of

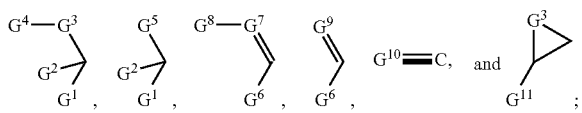

R[2] is

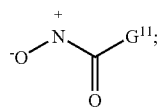

G[1] is selected from the group of H, halogen, CN, alkyl and substituted alkyl;
G[2] is selected from the group of H, alkyl, and substituted alkyl;
G[3] is selected from the group of O, S, and NZ[1];
G[4] is selected from the group of H, alkyl, substituted alkyl, OZ[2], NZ[2]Z[3], Z[2]C=O, Z[4]SO$_2$, and optionally substituted glycosyl;
G[5] is selected from the group of halogen, N$_3$, NCS, SH, CN, NC, N(Z[1])$_3$[+] and heteroaryl;
G[6] is selected from the group of H, alkyl, substituted alkyl, CF$_3$, OZ[5], SZ[5], and NZ[5]Z[6];
G[7] is CZ[7] or N;
G[8] is selected from the group of H, halogen, alkyl, substituted alkyl, OZ[10], SZ[10], NZ[10]Z[11];
G[9] is selected from the group of O, S, —NH—NH— and —N=N—;
G[10] is N or CZ[12];
G[11] is selected from the group of H$_2$N, substituted H$_2$N, alkyl, substituted alkyl, aryl, and substituted aryl;
Z[1], Z[6], Z[9], and Z[11] are independently selected from the group consisting of H, alkyl, substituted alkyl, acyl, and substituted acyl;
Z[2] is selected from the group of H, alkyl, substituted alkyl, aryl, substituted aryl, and heterocyclic;
Z[3], Z[5], Z[8], and Z[10] are independently selected from the consisting group of H, alkyl, substituted alkyl, acyl, substituted acyl, aryl, and substituted aryl;
Z[4] is selected from the group of alkyl, substituted alkyl, aryl, substituted aryl, and heterocyclic;
Z[7] is selected from the group of H, halogen, alkyl, substituted alkyl, aryl, substituted aryl, OZ[8], SZ[8], and NZ[8]Z[9]; and
Z[12] is selected from the group of H, halogen, alkyl, substituted alkyl, aryl, and substituted aryl;
with the proviso that when R[1] is

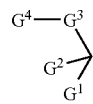

G[1], G[2], G[3] and G[4] cannot simultaneously have the following meanings: G[1] and G[2]=H, G[3] and G[4]=H or Z[2]C=O where Z[2]=alkyl, and with the proviso that when R[1] is

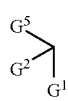

G[1], G[2] or G[5] cannot simultaneously gave the following meanings: G[1] and G[2]=H, and G[5]=F;

and any pharmaceutically acceptable salts, solvates, clathrates, hydrates, or prodrugs thereof;
b) a dibasic carboxylic acid; and
c) a dextran polymer.
39. The method according to claim 38 wherein said C-21 modified epothilone compound is of formula Ia:

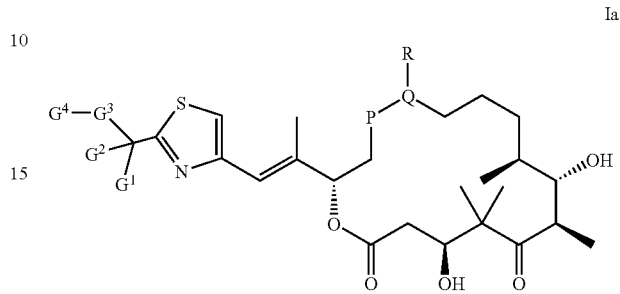

Ia wherein:
P-Q is a C,C double bond or an epoxide,
R is H or methyl,
G[1] is H, alkyl, substituted alkyl, or halogen,
G[2] is H, alkyl, or substituted alkyl,
G[3] is O, S, or NZ[1],
Z[1] is H, alkyl, substituted alkyl, acyl, or substituted acyl, and
G[4] is H, alkyl, substituted alkyl, OZ[2], NZ[2]Z[3], Z[2]C=O, Z[4]SO$_2$, or optionally substituted glycosyl,
Z[2] is H, alkyl, substituted alkyl, aryl, substituted aryl, or heterocyclic,
Z[3] is H, alkyl, substituted alkyl, acyl, or substituted acyl, and
Z[4] is alkyl, substituted alkyl, aryl, substituted aryl, or heterocyclic,
with the proviso that G[1], G[2], G[3] and G[4] cannot have simultaneously the following meanings: G[1] and G[2]=H atom, G[3]=O atom and G[4]=H atom or Z[2]C=O with Z[2]=alkyl;
and any pharmaceutically acceptable salts, solvates, clathrates, hydrates, or prodrugs thereof.
40. The method according to claim 39 wherein said C-21 modified epothilone compound is of formula Ib:

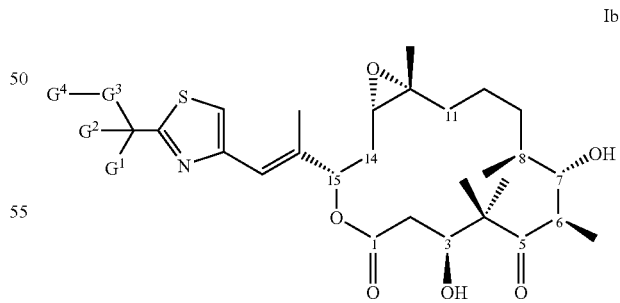

Ib wherein:
G[1] is H, alkyl, substituted alkyl, or halogen,
G[2] is H, alkyl, or substituted alkyl,
G[3] is O, S. or NZ[1],
Z[1] is H, alkyl, substituted alkyl, acyl, or substituted acyl,
G[4] is H, alkyl, substituted alkyl, OZ[2], NZ[2]Z[3], Z[2]C=O, Z[4]SO$_2$, or optionally substituted glycosyl, Z² is H, alkyl, substituted alkyl, aryl, substituted aryl, or heterocyclic, Z³ is H, alkyl, substituted alkyl, acyl, or substituted acyl, and Z⁴ is alkyl, substituted alkyl, aryl, substituted aryl, or heterocyclic, and any pharmaceutically acceptable salts, solvates, clathrates, hydrates, or prodrugs thereof.

41. The method according to claim 40 wherein said C-21 modified epothilone compound is of formula Ic:

Ic and any salts, solvates or hydrates thereof.

42. The method of claim 38 wherein said C-21 modified epothilone compound is administered orally in a dose of about 0.05 mg/kg to 200 mg/kg.

43. The method of claim 38 wherein said C-21 modified epothilone compound is administered intravenously at a dose of about 1 mg/m² to 100 mg/m².

44. The method of claim 38 wherein said C-21 modified epothilone compound is administered daily or weekly.

45. The method of claim 38 wherein said C-21 modified epothilone compound is administered once every week.

46. The method of claim 38 wherein said C-21 modified epothilone compound is administered once every three weeks.

47. The method of claim 38 wherein said C-21 modified epothilone compound is administered at least once a day for 3 days with a period of at least 4 days during which there is no treatment.

48. The method of claim 38 wherein said C-21 modified epothilone compound is administered at least once a day for 5 days with a period of at least 2 days during which there is no treatment.

49. The method of claim 38 wherein said C-21 modified epothilone compound is administered intravenously over a period of 15 minutes to 90 minutes.

50. The method of claim 38 wherein said patient has not previously been treated for cancer.

51. The method of claim 38 wherein said patient has previously been treated for cancer.

52. The method of claim 38 further comprising administering to said patient one or more additional agents to prevent nausea, vomiting, hypersensitivity, or gastric irritation.

53. The method of claim 41 wherein said C-21 modified epothilone compound is administered orally in a dose of about 0.05 mg/kg to 200 mg/kg.

54. The method of claim 53 wherein said C-21 modified epothilone compound is administered orally in a dose of about 0.05 mg/kg to 50 mg/kg.

55. The method of claim 41 wherein said C-21 modified epothilone compound is administered intravenously at a dose of about 1 mg/m² to 100 mg/m².

56. The method of claim 55 wherein said C-21 modified epothilone compound is administered intravenously at a dose of about 1 mg/m² to 70 mg/m².

57. The method of claim 56 wherein said C-21 modified epothilone compound is administered intravenously at a dose of about 10 mg/m² to 70 mg/m².

58. The method of claim 57 wherein said C-21 modified epothilone compound is administered intravenously at a dose of about 10 mg/m² to 65 mg/m².

59. The method of claim 58 wherein said C-21 modified epothilone compound is administered intravenously at a dose of about 50 mg/m².

60. The method of claim 58 wherein said C-21 modified epothilone compound is administered intravenously at a dose of about 30 mg/m².

61. The method of claim 41 wherein said C-21 modified epothilone compound is administered daily or weekly.

62. The method of claim 41 wherein said C-21 modified epothilone compound is administered once every week.

63. The method of claim 41 wherein said C-21 modified epothilone compound is administered once every three weeks.

64. The method of claim 41 wherein said C-21 modified epothilone compound is administered at least once a day for 3 days with a period of at least 4 days during which there is no treatment.

65. The method of claim 41 wherein said C-21 modified epothilone compound is administered at least once a day for 5 days with a period of at least 2 days during which there is no treatment.

66. The method of claim 41 wherein said C-21 modified epothilone compound is administered intravenously over a period of 15 minutes to 90 minutes.

67. The method of claim 41 wherein said patient has not previously been treated for cancer.

68. The method of claim 41 wherein said patient has previously been treated for cancer.

69. The method of claim 41 wherein said cancer is refractory to radiation therapy.

70. The method of claim 41 wherein said cancer is refractory to anticancer chemotherapy.

71. The method of claim 41 wherein said cancer is a solid tumor.

72. The method of claim 41 further comprising administering to said patient one or more additional agents to prevent nausea, vomiting, hypersensitivity, or gastric irritation.

73. The method of claim 72 wherein said agent is an $H_1$ or $H_2$ antihistamine.

74. The method according to claim 19 wherein step (d) comprising a primary drying stage conducted at a temperature in the range of from about −20° C. to about −10° C.

75. The method according to claim 74 wherein said step (d) further comprises a secondary drying stage conducted at a temperature in the range of from about −10° C. to about 30° C.

* * * * *

UNITED STATES PATENT AND TRADEMARK OFFICE
CERTIFICATE OF CORRECTION

PATENT NO. : 7,053,069 B2
APPLICATION NO. : 10/437103
DATED : May 30, 2006
INVENTOR(S) : Francis Y.F. Lee et al.

It is certified that error appears in the above-identified patent and that said Letters Patent is hereby corrected as shown below:

In the Claims:
Column 32, line 32, change "$R^2$" to -- $R^1$ --.
Column 35, line 32, change "$Z^4S_2$" to -- $Z^4SO_2$ --.
Column 35, line 60, change "$z^4$" to -- $Z^4$ --.
Column 36, line 12, change "Gand $G^2$=H,$G^3$=O and $G^4$=H or $Z^2$C=O where $Z^2$=alkyl" to -- $G^1$ and $G^2$=H, $G^3$=O and $G^4$=H or $Z^2$C=O where $Z^2$=alkyl --.
Column 36, line 23, change "Gand $G^2$=H" to -- $G^1$ and $G^2$=H --.
Column 37, line 21, change "G4" to -- $G^4$ --.
Column 38, line 24, change
"16S*]]3-2-[2[2-(aminomethyl)-4-thiazolyl]1-methyl-" to
-- 16S*]]-3-[2-[2-(aminomethyl)-4-thiazolyl]-1-methyl- --.
Column 39, line 5, change " $G^{10}$═C , " to -- $G^{10}$≡C ,--.
Column 39, line 58, change "$G^3$" to -- $G^3$=O --.

Signed and Sealed this

Seventeenth Day of October, 2006

JON W. DUDAS
*Director of the United States Patent and Trademark Office*